(12) United States Patent
Lee et al.

(10) Patent No.: US 8,727,993 B2
(45) Date of Patent: May 20, 2014

(54) APPARATUSES COMPRISING CATHETER TIPS, INCLUDING MECHANICALLY SCANNING ULTRASOUND PROBE CATHETER TIP

(75) Inventors: Warren Lee, Niskayuna, NY (US); Weston Blaine Griffin, Niskayuna, NY (US); Douglas Glenn Wildes, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 1663 days.

(21) Appl. No.: 11/624,344

(22) Filed: Jan. 18, 2007

(65) Prior Publication Data

US 2007/0167813 A1   Jul. 19, 2007

Related U.S. Application Data

(63) Continuation-in-part of application No. 11/289,926, filed on Nov. 30, 2005, now abandoned, and a continuation-in-part of application No. 11/330,377, filed on Jan. 11, 2006, now abandoned, and a continuation-in-part of application No. 11/329,815, filed on Jan. 11, 2006, and a continuation-in-part of application No. 11/330,378, filed on Jan. 11, 2006.

(51) Int. Cl.
   *A61B 8/14* (2006.01)
(52) U.S. Cl.
   USPC .......................................... 600/459; 600/437
(58) Field of Classification Search
   USPC ............... 600/437–469; 73/618–640
   See application file for complete search history.

(56) References Cited

U.S. PATENT DOCUMENTS

| 4,287,770 A | 9/1981 | Weyns |
| 5,181,514 A | 1/1993 | Solomon et al. |
| 5,240,003 A | 8/1993 | Lancee et al. |
| 5,413,107 A | 5/1995 | Oakley et al. |
| 5,464,016 A | 11/1995 | Nicholas et al. |
| 5,479,929 A | 1/1996 | Cooper et al. |
| 5,545,942 A | 8/1996 | Jaster et al. |
| 5,647,367 A | 7/1997 | Lum et al. |
| 5,699,805 A | 12/1997 | Seward et al. |

(Continued)

FOREIGN PATENT DOCUMENTS

WO   WO 98/33430 A2   8/1998

OTHER PUBLICATIONS

NL Search Report & Written Opinion—Jul. 27, 2009.

*Primary Examiner* — Sanjay Cattungal
(74) *Attorney, Agent, or Firm* — Seema S. Katragadda

(57) ABSTRACT

A catheter tip (50, 170, 750) is provided that is adapted for mating attachment to a catheter body (90, 300, 790). In an embodiment, the catheter tip (50, 170, 750) comprises a transducer array (32, 60, 110, 210, 710) in electrical communication with an interconnect (120, 220, 720) and in a mechanical driven relationship with an actuator (80, 730), also in the catheter tip (50, 170, 750), via a drive shaft (38, 82, 732). The transducer array (710) is encapsulated in a potting material body 711 providing a desired ultrasound acoustical transmission, A defined annular space 761 exists between an outer capsule 752 of the catheter tip 750 and the potting material body 711. Oscillating back and forth motion of the transducer array (32, 60, 110, 210, 710) provides ultrasonic imaging functionality that may include real time three-dimensional imaging. Other embodiments of the catheter tip (50, 170, 750) and methods of fabrication also are provided.

22 Claims, 19 Drawing Sheets

(56) References Cited

U.S. PATENT DOCUMENTS

| Patent/Pub No. | Date | Inventor(s) | Class |
|---|---|---|---|
| 5,721,463 A | 2/1998 | Snyder | |
| 5,957,850 A | 9/1999 | Marian, Jr. et al. | |
| 6,142,947 A | 11/2000 | Tran et al. | |
| 6,338,727 B1 | 1/2002 | Noda et al. | |
| 6,450,990 B1 | 9/2002 | Walker et al. | |
| 6,475,212 B2 | 11/2002 | Dobak, III et al. | |
| 6,589,182 B1 | 7/2003 | Loftman et al. | |
| 6,592,526 B1 | 7/2003 | Lenker | |
| 6,684,094 B1 | 1/2004 | Lehr et al. | |
| 6,709,392 B1 | 3/2004 | Salgo et al. | |
| 6,712,767 B2 | 3/2004 | Hossack et al. | |
| 6,905,466 B2 | 6/2005 | Salgo et al. | |
| 7,666,143 B2 * | 2/2010 | Wilser et al. | 600/463 |
| 7,798,971 B2 * | 9/2010 | Flesch et al. | 600/459 |
| 2001/0041842 A1 * | 11/2001 | Eberle et al. | 600/466 |
| 2002/0007120 A1 * | 1/2002 | Moore et al. | 600/466 |
| 2002/0049375 A1 | 4/2002 | Strommer et al. | |
| 2002/0055754 A1 | 5/2002 | Ranucci et al. | |
| 2002/0058873 A1 | 5/2002 | Seward et al. | |
| 2002/0072669 A1 | 6/2002 | Masters | |
| 2002/0087083 A1 | 7/2002 | Nix et al. | |
| 2002/0107447 A1 | 8/2002 | Suorsa et al. | |
| 2002/0156377 A1 | 10/2002 | Yock | |
| 2002/0188226 A1 | 12/2002 | White et al. | |
| 2002/0193690 A1 * | 12/2002 | Moore et al. | 600/466 |
| 2003/0004505 A1 * | 1/2003 | Bencini et al. | 606/41 |
| 2003/0032883 A1 | 2/2003 | Aksnes et al. | |
| 2003/0055308 A1 | 3/2003 | Friemel et al. | |
| 2003/0153833 A1 | 8/2003 | Bennett et al. | |
| 2003/0171667 A1 | 9/2003 | Seward | |
| 2003/0195496 A1 | 10/2003 | Maguire et al. | |
| 2003/0229286 A1 | 12/2003 | Lenker | |
| 2003/0229287 A1 | 12/2003 | Flesch et al. | |
| 2004/0015084 A1 | 1/2004 | Flesch et al. | |
| 2004/0019279 A1 | 1/2004 | White et al. | |
| 2004/0049148 A1 * | 3/2004 | Rodriguez et al. | 604/22 |
| 2004/0054289 A1 | 3/2004 | Eberle et al. | |
| 2004/0073114 A1 | 4/2004 | Oliver et al. | |
| 2004/0087859 A1 | 5/2004 | Yock | |
| 2004/0158151 A1 | 8/2004 | Ranucci et al. | |
| 2005/0015011 A1 | 1/2005 | Liard et al. | |
| 2005/0027198 A1 | 2/2005 | Couvillon, Jr. | |
| 2005/0121734 A1 | 6/2005 | Degertekin et al. | |
| 2005/0137520 A1 | 6/2005 | Rule et al. | |
| 2005/0203396 A1 | 9/2005 | Angelsen et al. | |
| 2005/0203416 A1 | 9/2005 | Angelsen et al. | |
| 2005/0209578 A1 | 9/2005 | Christian Evans et al. | |
| 2005/0215942 A1 | 9/2005 | Abrahamson et al. | |
| 2007/0038110 A1 * | 2/2007 | Flesch et al. | 600/459 |

* cited by examiner

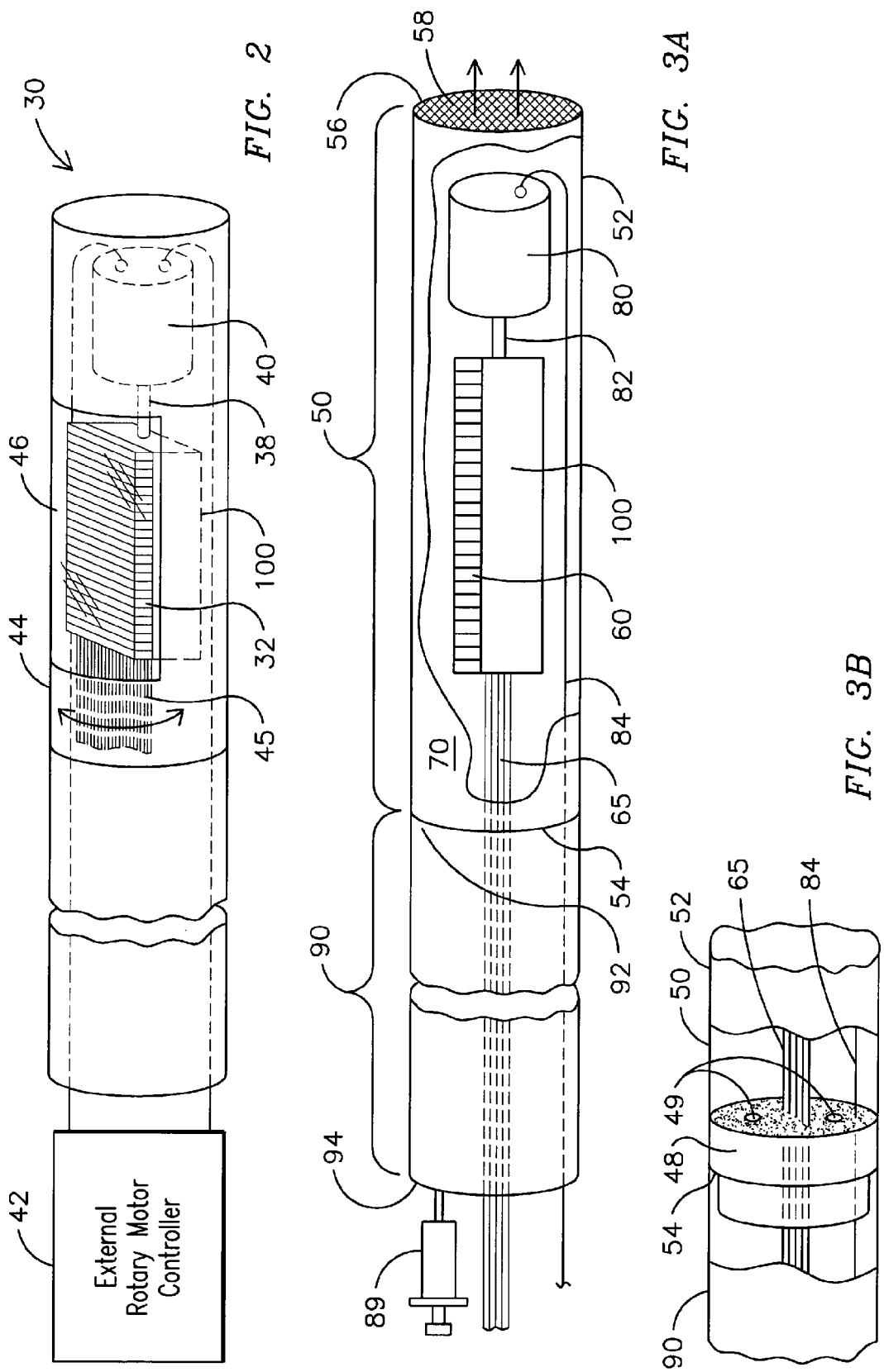

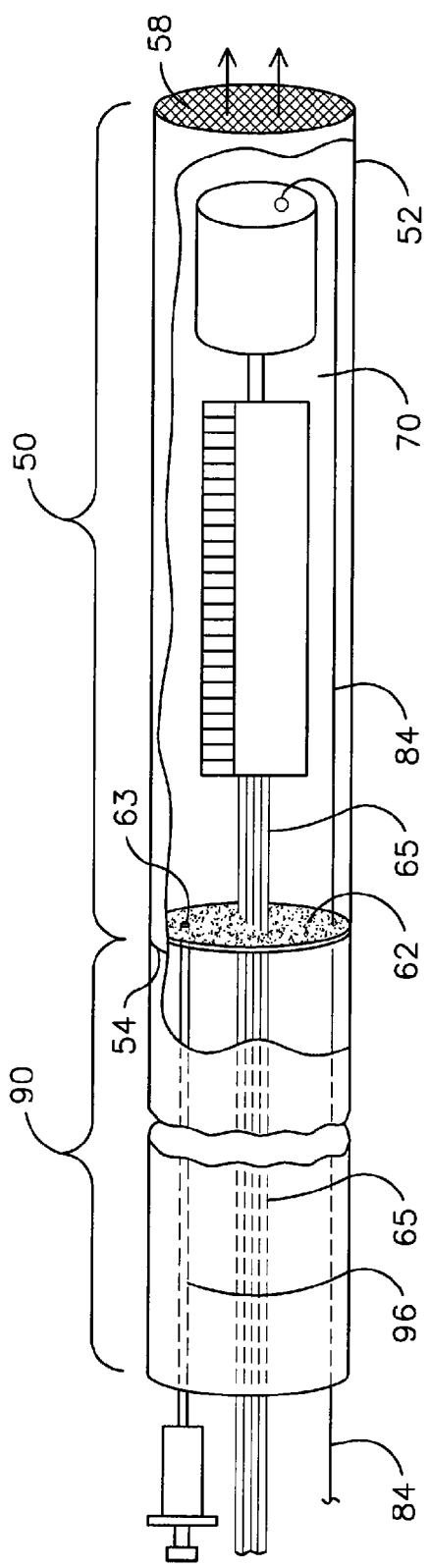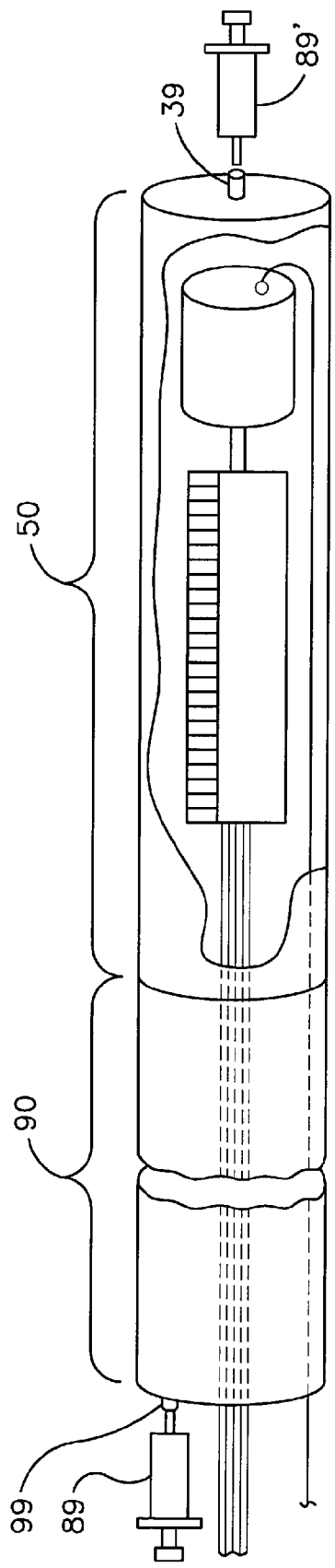
FIG. 4
FIG. 5

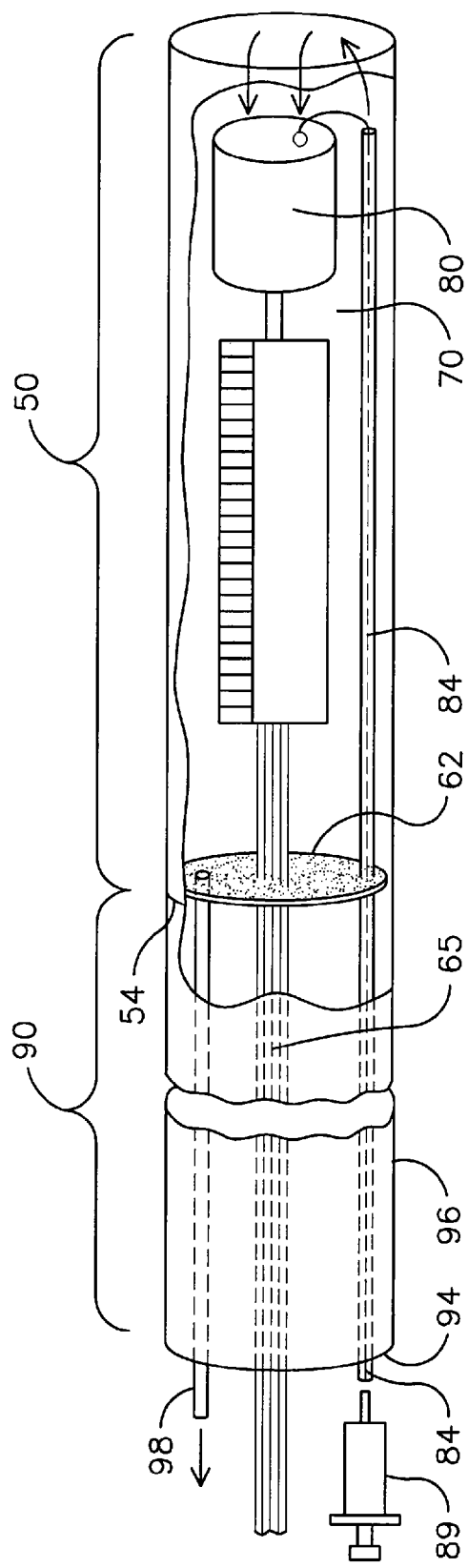
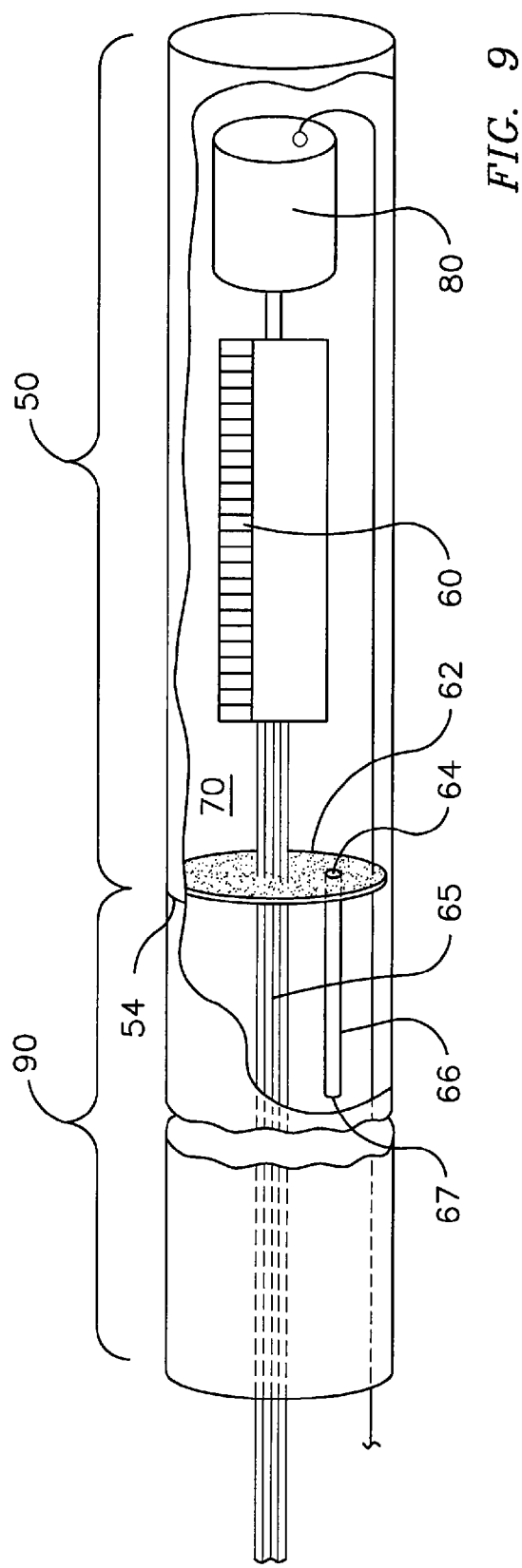

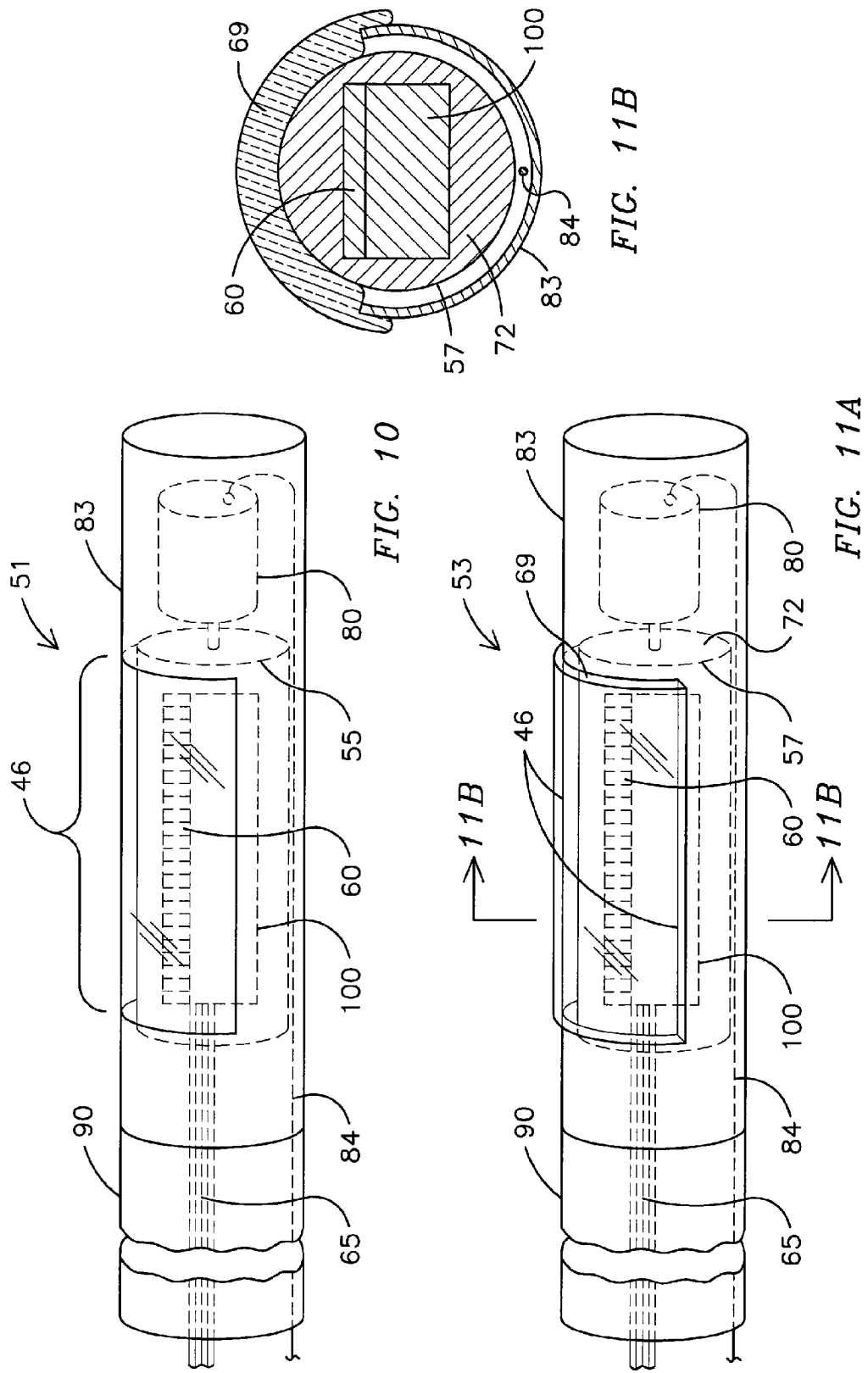

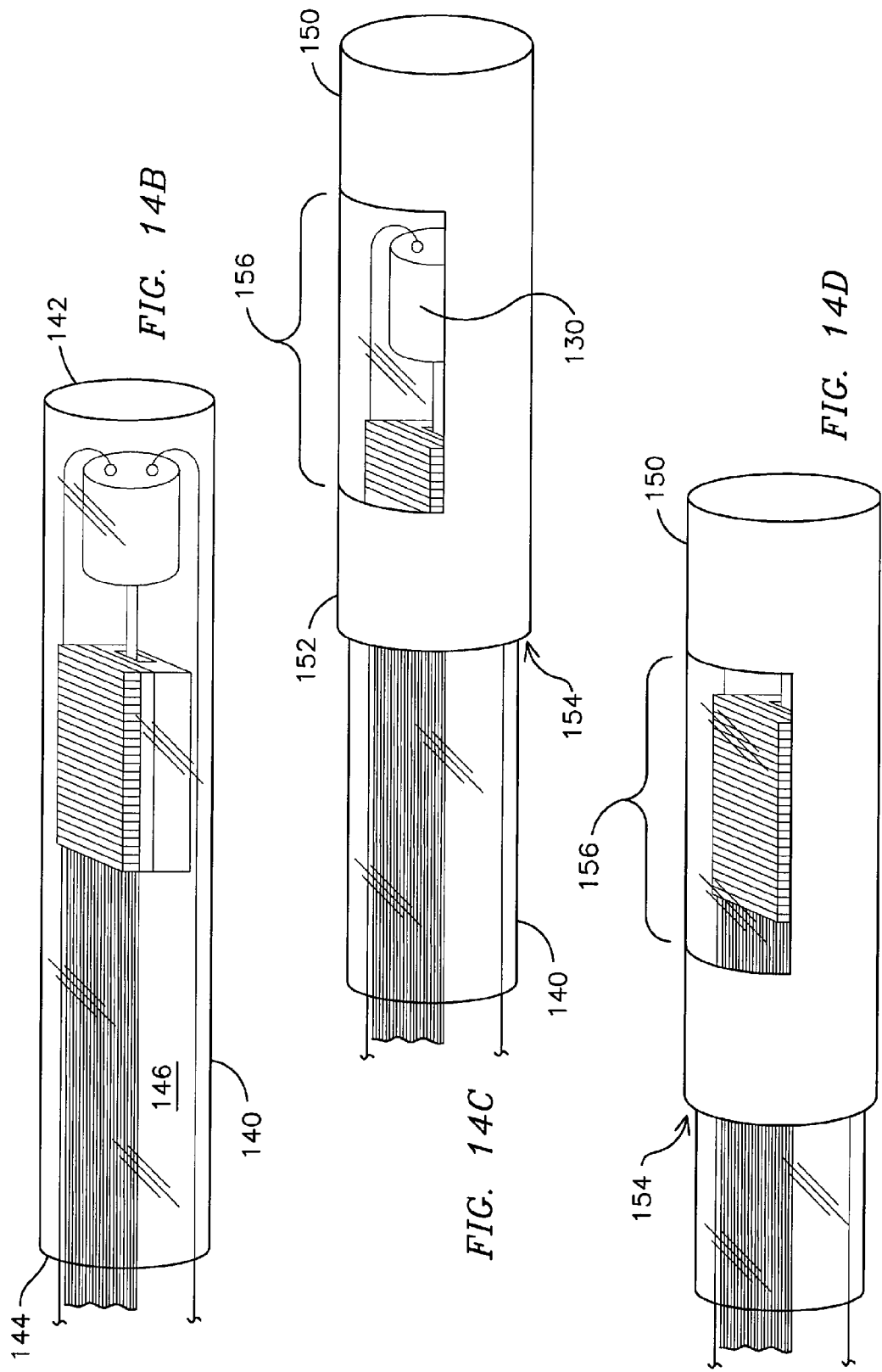

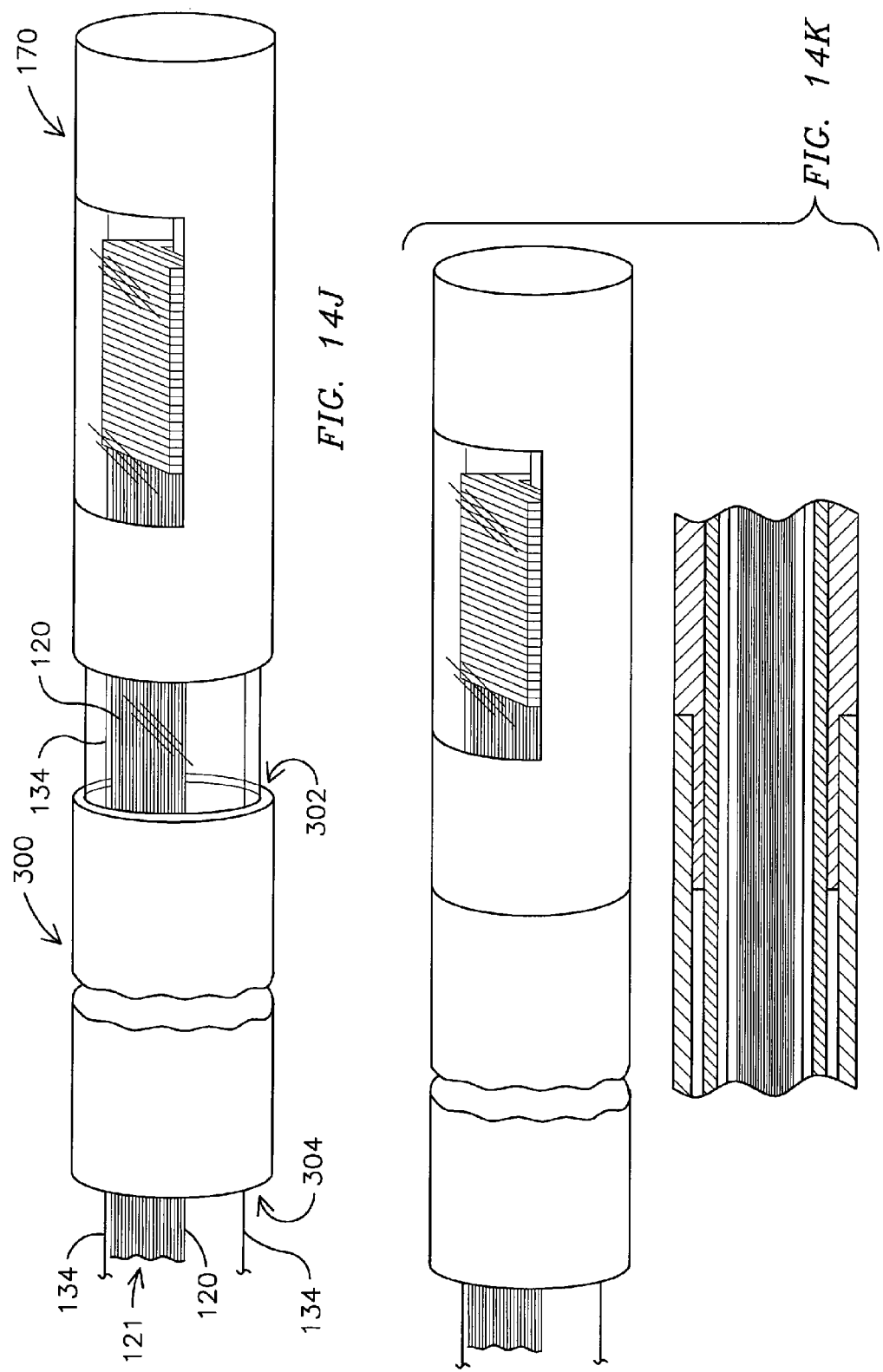

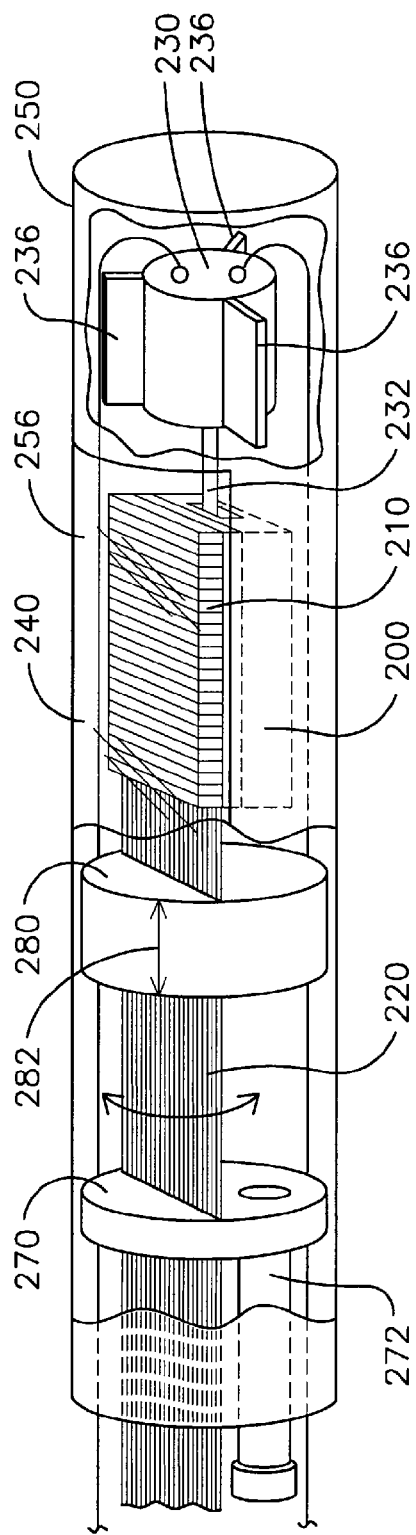
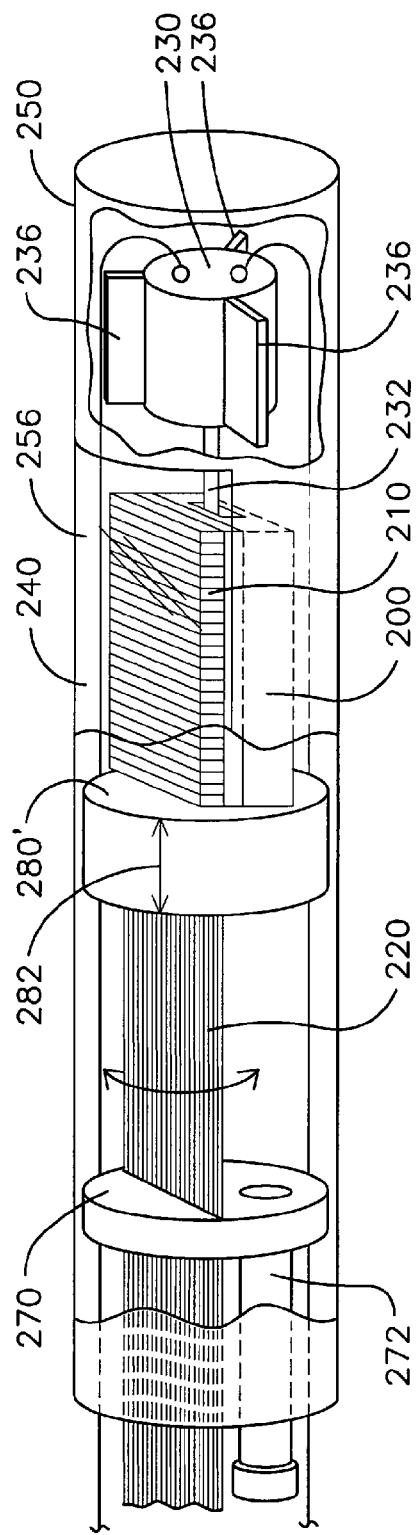

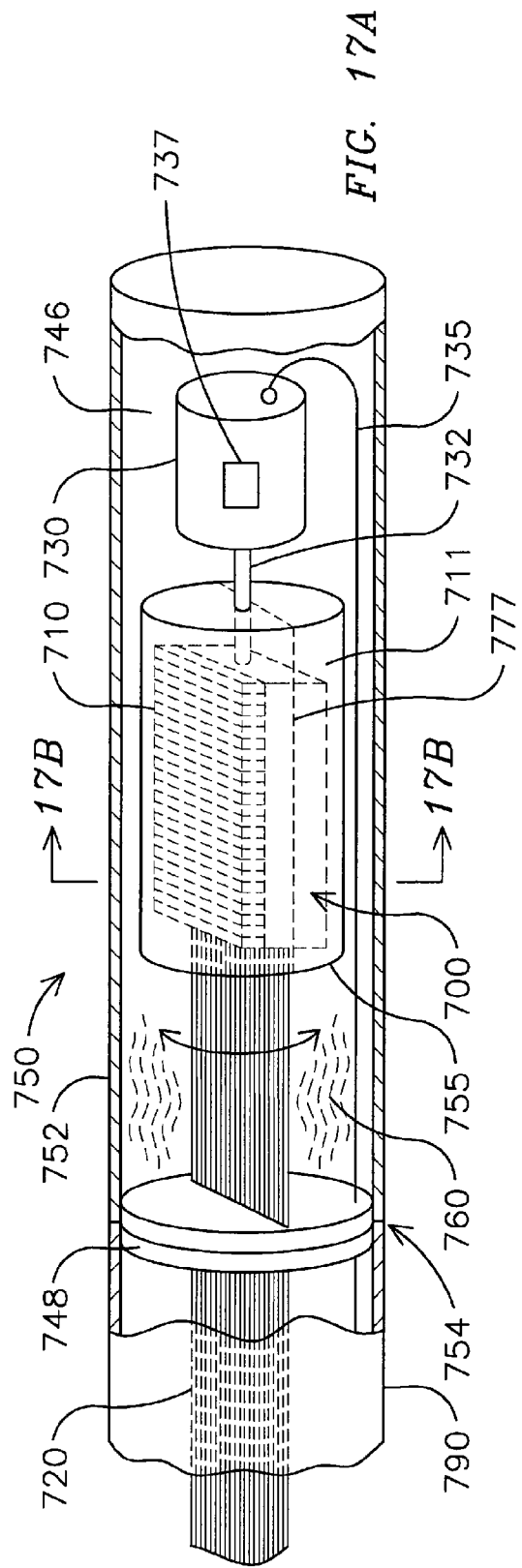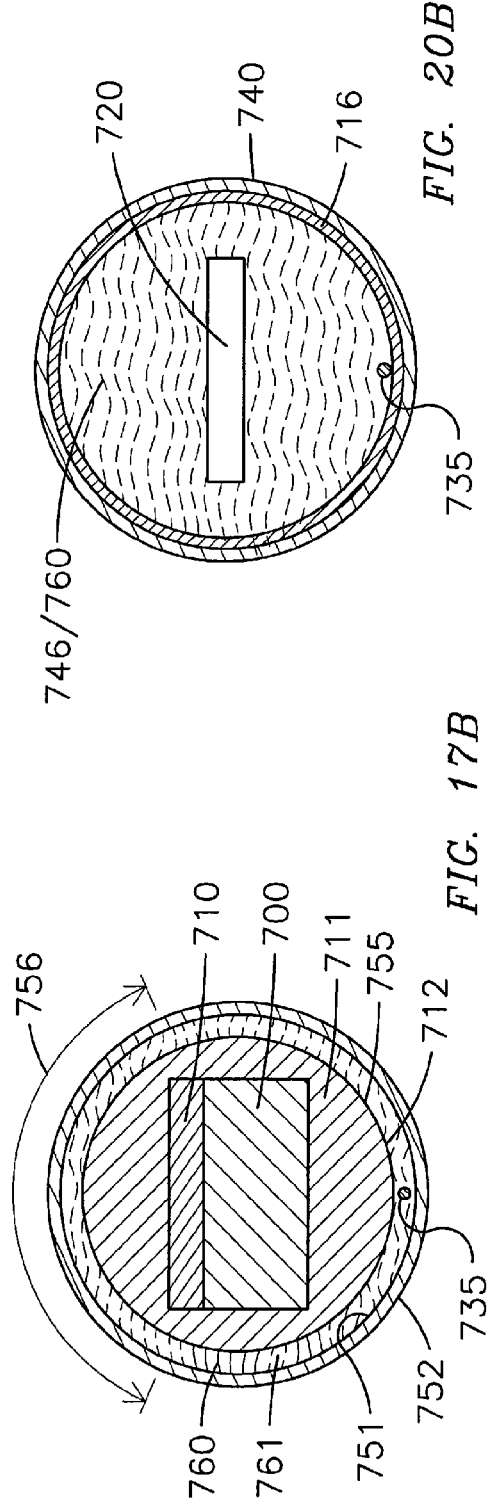

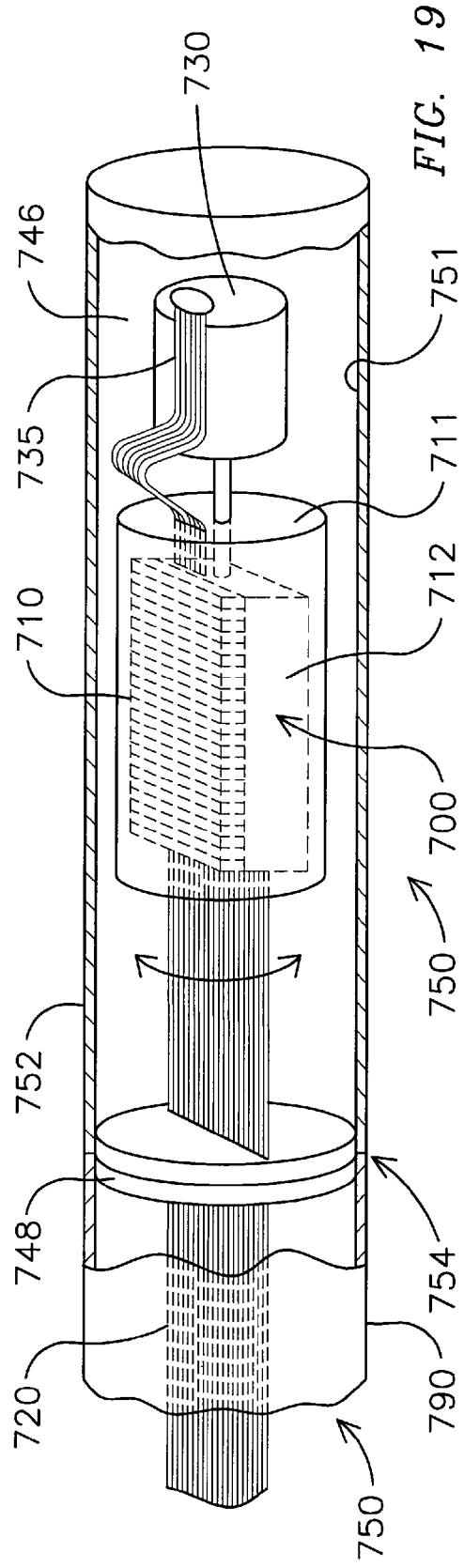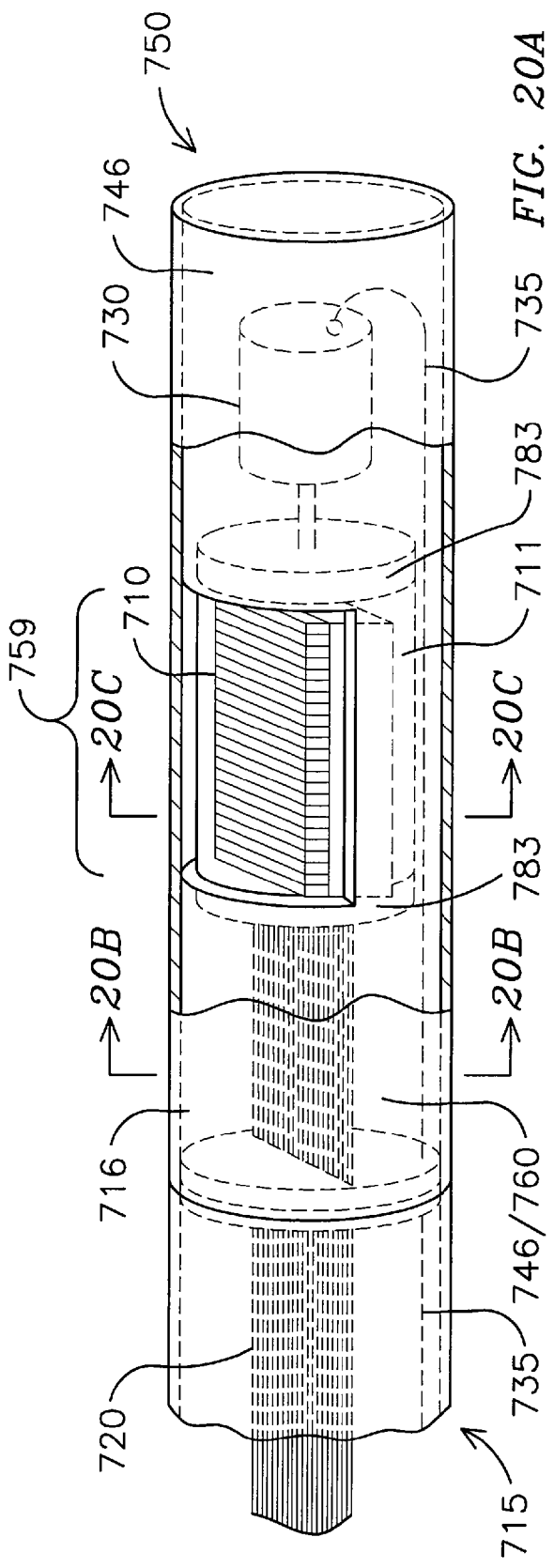

APPARATUSES COMPRISING CATHETER TIPS, INCLUDING MECHANICALLY SCANNING ULTRASOUND PROBE CATHETER TIP

CROSS-REFERENCE TO RELATED APPLICATIONS

This application is a continuation in part of application Ser. No. 11/289,926, filed Nov. 30, 2005 now abandoned. This application is also a continuation in part of the following Applications: application Ser. No. 11/330,377, filed Jan. 11, 2006, now abandoned and entitled Apparatus for Catheter Tips, Including Mechanically Scanning Ultrasound Probe Catheter Tip; application Ser. No. 11/329,815, filed Jan. 11, 2006, and entitled Method of Manufacture of Catheter Tips, Including Mechanically Scanning Ultrasound Probe Catheter Tip, And Apparatus Made By The Method, and application Ser. No. 11/330,378, filed Jan. 11, 2006, and entitled Apparatuses for Thermal Management of Actuated Probes, Such as Catheter Distal Ends.

BACKGROUND OF THE INVENTION

1. Field of the Invention

The field of the invention is ultrasonic probes, and particularly ultrasonic probes for catheter systems and provided in catheter tips for use with catheter systems.

2. Description of the Background Art

Ultrasound imaging of living human beings and animals has advanced in recent years in part due to advances in technologies related to computer data storage, transfer and analysis. Other advances, in the fields of component miniaturization and transducer design and composition, likewise have contributed to the advances in ultrasound imaging devices and methods.

Such advances have provided a foundation for development of various approaches to real time three dimensional ("RT3D") ultrasonic imaging, including those that use a catheter-based ultrasound probe. Real time three dimensional ultrasonic imaging from a unit housed in a catheter offers many advantages for conducting exacting diagnostic and interventional procedures. Accordingly, improvements in this field are expected to offer substantial cost effectiveness and other benefits for medical diagnostics and interventions.

However, cost-effective delivery of accurate and reliable catheter-based ultrasonic probes remains a challenge. Several approaches to meet this challenge are known. U.S. Pat. No. 5,699,805, as one example, teaches an underfluid catheter system catheter-based imaging device having an ultrasound transducer array positioned longitudinally along the catheter. The ultrasound transducer array is connected to a drive shaft that rotates the array relative to the catheter body, to generate a plurality of spatially related two-dimensional tomographic images of body structure adjacent the catheter. A control system includes a drive mechanism that, as stated, may be positioned within the catheter body or, as shown in the disclosed embodiment, is remotely located from the catheter body. In the latter, disclosed embodiment, the drive shaft extends through the entire length of the catheter body.

U.S. Pat. No. 6,592,526 teaches a catheter that includes an integral catheter tip that comprises an array of at least one transducer for transmitting ultrasound energy radially outward, and for receiving ultrasound energy. In an illustrated embodiment, a plurality of transducers are placed circumferentially about the tip, and each transducer transmits and receives ultrasound energy. Between the transducers are a plurality of blind spots or blind areas. Imaging proceeds by rotation of the array, such as by using sets of actuators, such as nitinol actuators. Some actuators move the array in the circumferential direction, and some actuators move the array axially forward and back. Strain gauges provide information about positioning, and an acoustic transmission fluid fills an area about the array of transducers. It is stated that three-dimensional volumetric images may be obtained by use of this catheter tip.

These approaches, however, do not solve the problems of providing an acoustic transmission medium into a catheter tip in a desired manner and time, nor of effectively cooling the transducer array and internal actuator to stay within prescribed temperature limits during use within a living person. Nor do these approaches address the opportunity to mass produce ultrasonic probe catheter tips that may be later combined with a number of different types of catheters, thus providing for greater economies.

Thus, notwithstanding advances in the field, there remains a need for cost-effective approaches to providing catheter tips comprising an ultrasound transducer array that is movable from an internal actuator such as an electromechanical actuator, and that is suitable for use in ultrasonic imaging that may include real time three-dimensional imaging.

BRIEF DESCRIPTION OF THE DRAWINGS

Features, aspects and advantages of embodiments of the present invention will become better understood when the following detailed description is read with reference to the accompanying drawings in which like characters represent like parts, wherein:

FIG. 2 is a side and internal view of an exemplary embodiment of a catheter tip comprising a rotating transducer array assembly, for use in the imaging system of FIG. 1.

FIG. 3A is a side view with cut-away, partially internal view of an exemplary embodiment of a catheter tip shown attached to a catheter body, which may be used in the imaging system of FIG. 1.

FIG. 3B is a side view with cut-away, partially internal view of the joining area between the catheter tip and catheter body of FIG. 3A, depicting a bulkhead which may be found in various embodiments.

FIG. 4 is a side view with cut-away, partially internal view of an alternative exemplary embodiment of a catheter tip shown attached to a catheter body, which may be used in the imaging system of FIG. 1.

FIG. 5 is a side view with cut-away, partially internal view of another alternative exemplary embodiment of a catheter tip shown attached to a catheter body, which may be used in the imaging system of FIG. 1, providing alternative approaches to filling the apparatus with an acoustic transmission medium.

FIG. 8 is a side view with cut-away, partially internal view of another alternative exemplary embodiment of a catheter tip shown attached to a catheter body, which may be used in the imaging system of FIG. 1, providing another alternative approach to filling the apparatus with an acoustic transmission medium.

FIG. 9 is a side view with cut-away, partially internal view of another alternative exemplary embodiment of a catheter tip shown attached to a catheter body, which may be used in the imaging system of FIG. 1, depicting a reservoir in communication with the defined space within the catheter tip.

FIG. 10 is a side and internal view of an alternative exemplary embodiment of a catheter tip, attached to a catheter body, and comprising a rotating cylinder in which is positioned a transducer array, for use in the imaging system of FIG. 1.

FIG. 11A is a side and internal view of another alternative exemplary embodiment of a catheter tip, attached to a catheter body, and comprising a rotating cylinder in which is positioned a transducer array, for use in the imaging system of FIG. 1.

FIG. 11B is a cross-sectional view of the embodiment of FIG. 11A taken along line B-B.

FIGS. 14A-H provide exemplary steps in the manufacture of catheter tips, not all of which need be practiced for various manufacture embodiments.

FIGS. 14J-L provide views related to assembly of catheter tips to catheter bodies.

FIGS. 15A-D provide side views with cut-away, partially internal views of several alternative approaches for providing additional mechanical supports to structures in catheter tip embodiments of the present invention.

FIG. 17A is a side view with cut-away, partially internal view of an additional exemplary embodiment of a catheter tip providing an alternative arrangement of components therein.

FIG. 17B is a cross-section view taken at line B-B of FIG. 17A.

FIG. 19 is a side view with cut-away, partially internal view of a catheter tip similar to that of FIGS. 17A and 17B, with a motor interconnect provided between a transducer assembly and a micromotor.

FIG. 20A is a side view with cut-away, partially internal view of a catheter tip comprising a rigid capsule having a cut-out section.

FIG. 20B is a cross-section view taken along the line B-B of FIG. 20A.

DETAILED DESCRIPTION OF EMBODIMENTS OF THE INVENTION

Figure 1:
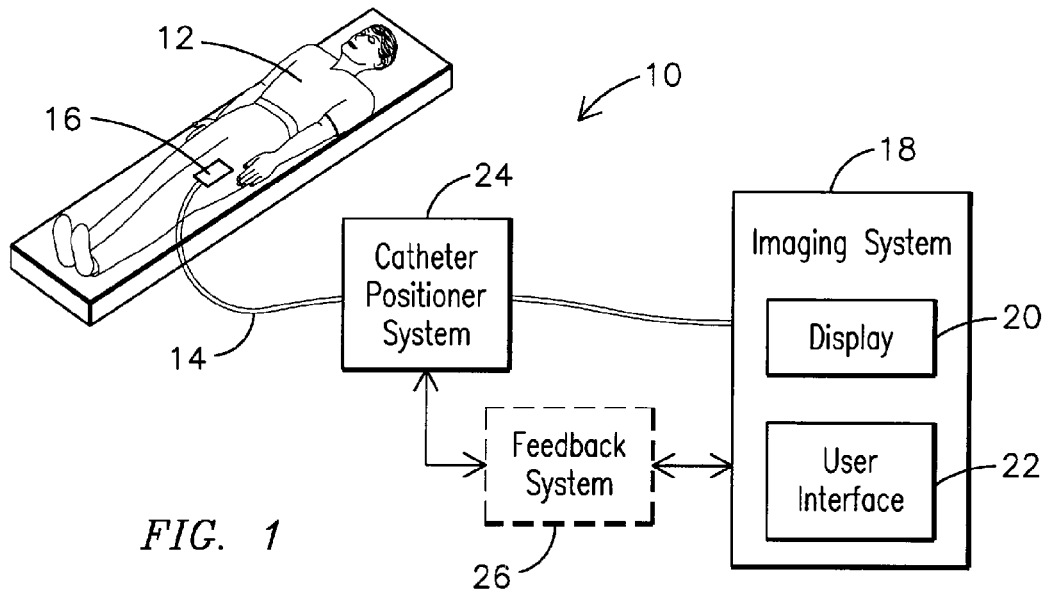
FIG. 1 is a block diagram of an exemplary catheter imaging and therapy system, in accordance with and/or adaptable to utilize aspects of the present apparatus and methods.

A number of problems limit the advance of more cost-effective and more accurate catheter-based ultrasound imaging. One problem relates to the present lack of a separate, attachable catheter tip assembly comprising ultrasonic imaging capability wherein that tip assembly is adapted for mating attachment to one or more types of catheter bodies. Such catheter tip assembly may advantageously be provided with a relatively short interconnect that attaches to electrical conduits at a distal end of a catheter body, or with a longer interconnect that passes through the catheter body and connects to signaling and control components of a catheter ultrasound system. Such catheter tips, as are described herein, and their methods of manufacture, broaden alternatives for assembly and for filling such catheter tips with an acoustic transmission medium.

Other or related problems solved herein relate to provision of an acceptable acoustic transmission medium between a rotatably moving ultrasound transducer array and an outer surface of the catheter tip, to arrangement of major components within a catheter tip to reduce catheter tip diameter, and to development of assembly methods for catheter tips that may provide flexible alternatives for assembly with catheter bodies and integrated catheter systems.

Various embodiments of the invention solve such problems through alternative approaches. Ultrasonic imaging catheter tip assemblies are provided that may be matingly attached to one or more selected catheter bodies, and used therewith, and that may comprise an actuator for providing a desired motion to a driven ultrasound transducer or transducer array. Some embodiments of such catheter tip assemblies provide solutions to establish and maintain an acceptable sound transmission medium within the catheter tip. That is, in some such embodiments an acoustic transmission medium may be sealed within the catheter tip during tip manufacture, or alternatively may be provided from an external source prior to use, such as through the catheter body. Other embodiments solve that problem by non-fluid media that may comprise a solid material, a gel, or a fluid permeable membrane.

Some embodiments solve the assembly method problems by providing methods of fabrication for catheter tips comprising ultrasonic probes, by providing methods of assembly of the same to catheters, and by providing specific catheter tips manufactured in accordance with those methods.

Thus, a number of embodiments are provided that combine a selected one of a number of construction embodiments, and utilize a selected one of a number of fluid management embodiments. For example, a catheter tip embodiment may comprise a metal outer capsule with a cut-out acoustic window (additionally comprising an inner or an outer plastic sheath), or may comprise a plastic outer capsule that has desired acoustic transmission properties. Fluid management embodiments for any of such catheter tip construction embodiments may include:

1. Fluid system is open to the body into which a catheter tip may be inserted. These embodiments include systems in which a fluid flushes through the catheter body and the catheter tip, or only through a sealed catheter tip.

2. Fluid system is closed, so fluid does not pass to the body from the catheter tip. Various embodiments are provided in which the catheter tip is filled either during manufacture or later, prior to use.
3. The catheter tip does not require added fluid, but instead may comprise a membrane or other system providing for a desired acoustic transmission path.

Various embodiments described herein comprise an electromechanical actuator positioned at the distal end of the catheter tip, more distal than a transducer array that it moves. However, the following descriptions are meant to be illustrative of various embodiments but are not meant to be limiting.

FIG. 1 is a block diagram of an exemplary ultrasound imaging system 10 for use in imaging and providing therapy to one or more regions of interest in accordance with aspects of the present technique. The system 10 may be configured to acquire image data from a patient 12 via a catheter 14. As used herein, "catheter" is broadly used to include conventional catheters, endoscopes, laparoscopes, transducers, probes or devices adapted for imaging as well as adapted for applying therapy. Further, as used herein, "imaging" is broadly used to include two-dimensional imaging, three-dimensional imaging, or preferably, real-time three-dimensional imaging. Further, as used herein, "fluid" may be interpreted broadly to include a liquid or a gel. Reference numeral 16 is representative of a portion of the catheter 14 disposed inside the body of the patient 12. This portion 16 may comprise a catheter tip as is disclosed and described in later figures.

In certain embodiments, an imaging orientation of the imaging and therapy catheter 14 may include a forward viewing catheter or a side viewing catheter. However, a combination of forward viewing and side viewing catheters may also be employed as the catheter 14. Catheter 14 may include a real-time imaging and therapy transducer (not shown). According to aspects of the present technique, the imaging and therapy transducer may include integrated imaging and therapy components. Alternatively, the imaging and therapy transducer may include separate imaging and therapy components. The transducer in an exemplary embodiment is a 64 element one-dimensional (1D) transducer array and will be described further with reference to FIG. 2. It should be noted that although the embodiments illustrated are described in the context of a catheter-based transducer, other types of transducers such as transesophageal transducers or transthoracic transducers are also contemplated.

In accordance with aspects of the present technique, the catheter 14 may be configured to image an anatomical region to facilitate assessing need for therapy in one or more regions of interest within the anatomical region of the patient 12 being imaged. Additionally, the catheter 14 may also be configured to deliver therapy to the identified one or more regions of interest. As used herein, "therapy" is representative of ablation, percutaneous ethanol injection (PEI), cryotherapy, and laser-induced thermotherapy. Additionally, "therapy" may also include delivery of tools, such as needles for delivering gene therapy, for example. Additionally, as used herein, "delivering" may include various means of guiding and/or providing therapy to the one or more regions of interest, such as conveying therapy to the one or more regions of interest or directing therapy towards the one or more regions of interest. As will be appreciated, in certain embodiments the delivery of therapy, such as RF ablation, may necessitate physical contact with the one or more regions of interest requiring therapy. However, in certain other embodiments, the delivery of therapy, such as high intensity focused ultrasound (HIFU) energy, may not require physical contact with the one or more regions of interest requiring therapy.

The system 10 may also include a medical imaging system 18, which may comprise an ultrasound control system, that is in operative association with the catheter 14 and configured to image one or more regions of interest. The imaging system 10 may also be configured to provide feedback for therapy delivered by the catheter or separate therapy device (not shown). Accordingly, in one embodiment, the medical imaging system 18 may be configured to provide control signals to the catheter 14 to excite a therapy component of the imaging and therapy transducer and deliver therapy to the one or more regions of interest. In addition, the medical imaging system 18 may be configured to acquire image data representative of the anatomical region of the patient 12 via the catheter 14.

As illustrated in FIG. 1, the imaging system 18 may include a display area 20 and a user interface area 22. However, in certain embodiments, such as in a touch screen, the display area 20 and the user interface area 22 may overlap. Also, in some embodiments, the display area 20 and the user interface area 22 may include a common area. In accordance with aspects of the present technique, the display area 20 of the medical imaging system 18 may be configured to display an image generated by the medical imaging system 18 based on the image data acquired via the catheter 14. Additionally, the display area 20 may be configured to aid the user in defining and visualizing a user-defined therapy pathway. It should be noted that the display area 20 may include a three-dimensional display area. In one embodiment, the three-dimensional display may be configured to aid in identifying and visualizing three-dimensional shapes. It should be noted that the display area 20 and respective controls could be remote from the patient, for example a control station and a boom display disposed over the patient.

Further, the user interface area 22 of the medical imaging system 18 may include a human interface device (not shown) configured to facilitate the user in identifying the one or more regions of interest for delivering therapy using the image of the anatomical region displayed on the display area 20. The human interface device may include a mouse-type device, a trackball, a joystick, a stylus, or a touch screen configured to facilitate the user to identify the one or more regions of interest requiring therapy for display on the display area 20.

As depicted in FIG. 1, the system 10 may include an optional catheter positioning system 24 configured to reposition the catheter 14 within the patient 12 in response to input from the user. The catheter positioning system 24 may be of any type known in the art, or disclosed in the parent application, U.S. patent application Ser. No. 11/289,926, filed Nov. 30, 2005, which is incorporated by reference for this and for teachings related to the interconnect. Moreover, the system 10 may also include an optional feedback system 26 that is in operative association with the catheter positioning system 24 and the medical imaging system 18. The feedback system 26 may be configured to facilitate communication between the catheter positioning system 24 and the medical imaging system 18.

FIG. 2 is an illustration of an exemplary embodiment of a rotating transducer array assembly 30 for use in the imaging system of FIG. 1, which may be incorporated into catheter tips as described herein. As shown, the transducer array assembly 30 comprises a transducer array 32, a micromotor 40 (a type of an actuator), which may be internal or external to the space-critical environment, a drive shaft 38 or other mechanical connections between micromotor 40 and the transducer array 32. The assembly 30 further includes a catheter housing 44 for enclosing the transducer array 32, the micromotor 40, an interconnect 45 and the drive shaft 38. In this embodiment, the transducer array 32 is mounted on drive shaft 38 and the transducer array 32 is rotatable with the drive shaft 38. Further in this embodiment, a motor controller 42 and micromotor 40 control the motion of transducer array 32 for rotating the transducer. In an embodiment, the micromotor 40 is placed in proximity to the transducer array 32 for rotating the transducer array 32 and drive shaft 38 and the motor controller 42 is used to control and send signals to the micromotor 40. Interconnect 45 refers to, for example, cables and other connections coupled between the transducer array 32 and the imaging system shown in FIG. 1 for use in receiving/transmitting signals between the transducer and the imaging system. In an embodiment, interconnect 45 is configured to reduce its respective torque load on the transducer and motion controller due to a rotating motion of the transducer which will be described in greater detail with reference to FIG. 3A below. It is noted that transducer array 32 may be incorporated, as shown in FIG. 2, into a transducer assembly 100, but this arrangement is not meant to be limiting.

Catheter housing 44 is of a material, size and shape adaptable for internal imaging applications and insertion into regions of interest. The catheter housing 44 may be integral, or may be comprised of a catheter tip attachable to a catheter body as described herein. The catheter housing 44 further comprises an acoustic window 46. Acoustic window 46 is provided to allow coupling of acoustic energy from the rotating transducer array 32 to the region or medium of interest. The window 46 and fluid between the window 46 and the transducer array 32 allow efficient transmission of acoustic energy from the array 32, which is inside the transducer array assembly 30, to the outside environment. In some embodiments, the window 46 and the fluid have impedance (acoustic) of about 1.5 MRayls. In an embodiment, the motor controller is external to the catheter housing as shown in FIG. 2. In another embodiment, the motor controller 42 is internal to the catheter housing. It is to be appreciated that micromotors and motor controllers are becoming available in miniaturized configurations that may be applicable to embodiments of the present invention. Micromotor and motor controller dimensions are selected to be compatible with the desired application, for example to fit within the catheter for a particular intracavity or intravascular clinical application. For example, in ICE applications, the catheter housing and components contained therein may be in the range of about 1 mm to about 4 mm in diameter.

Various embodiments of ultrasound probe catheter tips comprise a cylindrical outer capsule, such as a plastic outer housing, within which are arranged a more distally positioned electromechanical actuator connected by a drive shaft to a more proximally positioned transducer array, which is connected to an interconnect adapted to communicate with an imaging or therapy system. This arrangement is described herein and is depicted in various figures. However, this arrangement is not meant to be limiting, and other arrangements exist for components within a catheter tip embodiment of the invention. In order to eliminate air bubbles that may interfere with ultrasonic imaging, and in order to maintain a desired acceptable temperature of the probe and the transducer array, a number of approaches are employed. Some of these approaches involve fluid passage through both the catheter tip and a catheter body to which it is attached, thereby providing a catheter system. The following section describes and illustrates a number of these approaches by providing specific embodiments as examples of such approaches.

In various embodiments, an actuator, such as an electromechanical actuator, is positioned more distal than a transducer array that it moves, thus eliminating such drive shaft through the catheter body. This arrangement, generally depicted in FIG. 2 for any type of actuator, allows more space for an interconnect that delivers signals and receives data from the transducer array. While not meant to be limiting, this arrangement is utilized to exemplify various embodiments in FIGS. 3 to 9 that are directed to catheter tips, connection of these to catheter bodies, and to different arrangements for providing acoustic transmission fluid to catheter tips.

FIG. 3A depicts a side cut-away view of one embodiment of the invention. A catheter tip 50 is shown in a joined relationship with an end 92 of a catheter body 90. The catheter body 90 extends for a length, represented by the breaks in the figure, and may, in operation, connect at its proximal end 94 to related components of a medical imaging system as is described above. The catheter tip 50 is comprised of a cylindrical outer capsule 52 extending from a joining end 54, for attachment to the catheter body 90, to a distal end 56, a transducer array 60, and a defined space 70 between the cylindrical outer capsule 52 and ends 54, 56 and the transducer array 60 positioned in a transducer assembly 100. An actuator 80 is in mechanical driving relationship, via a drive shaft 82 connecting to the transducer assembly 100, with the transducer array 60. Although depicted as having only 24 divisions, in an exemplary embodiment transducer array 60 is a 64-element 1D array having 0.110 mm azimuth pitch, 2.5 mm elevation, and 6.5 MHz frequency. Such exemplary embodiment, however, is not meant to be limiting. Also, while transducer array 60 is positioned in a transducer array assembly 100, this is not meant to be limiting.

An interconnect 65 communicates with the transducer array 60 and may extend to or through the catheter body 90. That is, the interconnect 65 may extend only to meet an electrical connection at the joining end 92 of the catheter body 90, communicating there to a separate electrical conduit that passes through the catheter body 90. Alternatively a longer interconnect 65 may be sized to pass through the catheter body 90 to connect to signaling and control components of a catheter ultrasound system (not shown). For example, an interconnect of a catheter tip assembly as provided herein may have a length of at least 50 centimeters, or between about 50 and 200 centimeters, or between about 50 and 150 centimeters, or between about 80 and about 120 centimeters, and all subranges therebetween.

Also, at least one conductive wire 84 communicates with the actuator 80 and passes through the catheter body 90 to an external rotary motor control (not shown). Although not shown in the figure, an alternative is for such conductive wire to be part of the interconnect 65. The catheter tip 50 comprises an aperture 58 at the catheter tip distal end 56 that is effective for fluid passage. The joining end 54 is not sealed and this provides for passage of a fluid from the catheter body 90 through the defined space 70 to the aperture 58. A syringe 89, is shown to depict one of any number of alternative sources and devices known to those skilled in the art that may be used to inject, or to pump, fluid into the catheter body 90. Other alternatives include controlled micropumps.

An optional bulkhead 48 is depicted in FIG. 3B, and may be an optional component of this and other embodiments such as are described in relation to figures. Such bulkhead 48 may or may not be provided, and when provided, may or may not act as a sealing joint, wherein a sealing joint provides a fluid-tight barrier between a catheter tip and an adjoined catheter body. In the embodiment depicted in FIG. 3B, the bulkhead 48, which is a component of catheter tip 50, fills a space at joining end 54 within outer capsule 52. The bulkhead in FIG. 3B also is adapted to partially extend into catheter body 90, but this is not meant to be limiting. Alternatively, a bulkhead more generally may end at a joining end of a catheter tip (such as joining end 54 in FIG. 3A), or may be placed in a catheter tip more distally from a joining end (e.g., see FIG. 15A). A primary purpose for a bulkhead is to provide mechanical support for cables, such as interconnect 65. The bulkhead in such role may constrain the rotating or other motion, caused by an actuator, of such cables further proximal of itself, while also constraining cable motion, such as from bending of the catheter body, further distally of the bulkhead. This thereby provides a strain relief for the cables, such as interconnect 65, that may require a certain length and flexibility in a catheter tip, in that a tight restraint through the bulkhead would isolate the section of interconnect in the catheter tip from a second section in the catheter body. This strain relief and isolation may be important for catheter tips that are attached to steering catheter bodies that may experience bending during operation (wherein the bending would affect the interconnect section in the catheter tip but for the bulkhead). It is appreciated that glue or other adhesive around cables, such as interconnect 65, and extending to all or a portion of an outer capsule, such as 52, may comprise a bulkhead as that term is used herein. Also, it is appreciated that conductive wires such as 84, and the like, passing to an actuator in the catheter tip may be appropriately passed through a bulkhead.

As indicated above, the bulkhead may or may not, depending on design objectives, provide a fluid seal. In the embodiment depicted in FIG. 3B, two passages 49 provide for fluid communication between the catheter body 90 and the catheter tip 50. However, other bulkheads restrict passage of fluids, and it also is appreciated that a 'seal' as used herein may provide a fluid-impermeable barrier without providing mechanical support, and therefore embodiments may comprise either a seal, a bulkhead that allows passage of fluids through it, or a bulkhead that comprises or is adjacent to a seal. Also, a bulkhead may function to add strength to the catheter tip and to the joint between the catheter tip and a catheter body. Thus, in various embodiments a bulkhead of a catheter tip may be used to provide strain relief, may have cables passing through it, and may have passages through it to allow fluid flow.

The defined space 70 is adapted to receive a suitable acoustic transmission medium (not shown in FIG. 3A) selected from a liquid type fluid. The embodiment of FIG. 3A provides a solution to the problem of filling a catheter tip such as catheter tip 50 with an acoustic transmission liquid because the liquid fluid may be added to the proximal end 94 of catheter body 90 shortly prior to use, such as with syringe 89 or from another source (not shown), rather than during manufacture, and may pass out of the aperture 58. Distal aperture 58 is depicted as a screen mesh with a plurality of openings, and may alternatively comprise one or a smaller number of more discrete openings. In this embodiment the fluid and all exposed components within the catheter body 90 and catheter tip 50 are required to be biocompatible.

However, in this approach the entire catheter assembly comprising 90 and 50 is not rendered inoperable had there been an air bubble entrapped above the transducer array 60. If a bubble is detected, such as by inference from poor image quality, additional fluid can be added from the syringe 89 at proximal end 94 to purge such bubble. Appropriate caution would need to be exhibited in flushing an air bubble from the aperture 58 when the catheter tip 50 is within a body lumen such as a blood vessel. Also, this approach is viewed to provide a longer potential shelf life, as the catheter tip 50 is not shipped and stored while filled with a liquid fluid.

Components described above in FIGS. 3A and 3B are depicted in the following figures, and to avoid burdening the reader with repetitious description, only components relevant to differences in these embodiments, or to their operation, are discussed and noted in the figures.

Another embodiment is depicted in FIG. 4. This is similar to FIG. 3A, except that a seal 62 is provided at the joining end 54 that is effective to prevent passage of fluids between the catheter tip 50 and the catheter body 90. The seal 62 extends from the cylindrical outer capsule 52 and seals around the interconnect 65 and the at least one conductive wire 84.

The catheter body 90 comprises a defined passageway 96 for fluid ending at an aperture 63 in the seal 62, wherein a pathway for fluid exists through the defined passageway 96, through the seal aperture 63, and through the defined space 70 to the distal aperture 58. This approach obviates the need to have all components of the catheter body 90 be biocompatible.

Although not depicted explicitly in FIG. 4, it is appreciated that the defined passageway 96, which also may be referred to as a "fill tube," may or may not, depending of a desired design approach, contain some or all of the interconnect and actuator conductive wires up to the seal 62. Also, it is noted that instead of the seal 62, in alternative embodiments (not shown in FIG. 4) a bulkhead may be used.

In such embodiments in which the fluid may pass into a body space, the fluid is required to be biocompatible. By this is meant that the fluid is approved for intravenous or intracardiac injection. One example of biocompatible fluids is sterile saline.

Another embodiment, depicted in FIG. 5, is designed so as to not pass fluid to a body space during use in a body. In FIG. 5 catheter tip 50 and catheter body 90 each comprise a respective sealable aperture 39, 99 adapted for filling the catheter body 90 and the catheter tip 50 with the suitable acoustic transmission medium. No internal seal exists between the catheter tip 50 and the catheter body 90. One or both of the sealable apertures 39, 99 may be utilized during a filling procedure. For example, a source 89 of acoustic transmission medium may be connected to aperture 99 and the medium enters the catheter body 90, and then fills the catheter tip 50, which may be positioned at a higher relative elevation. Air purges through sealable aperture 39 until all air exits, at which time both sealable apertures 39, 99 are sealed. Alternatively, fluid may be provided through sealable aperture 39 from syringe 89' or other source, air purged through sealable aperture 99, and both such apertures 39, 99 may then be sealed.

Figure 6:
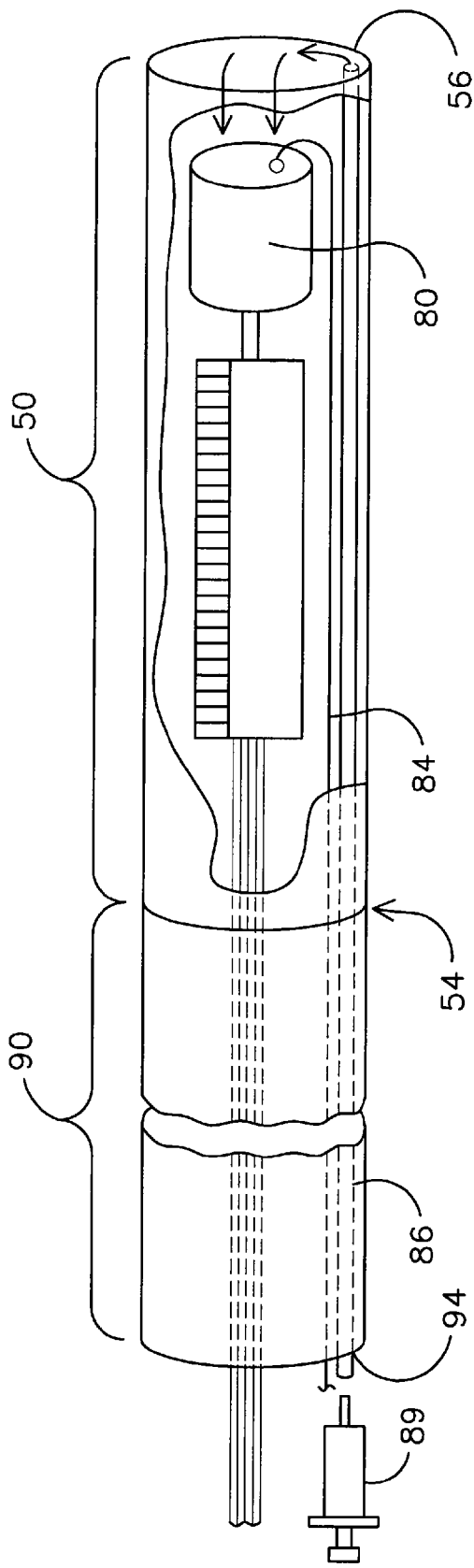
FIG. 6 is a side view with cut-away, partially internal view of another alternative exemplary embodiment of a catheter tip shown attached to a catheter body, which may be used in the imaging system of FIG. 1, providing an alternative approach to filling the apparatus with an acoustic transmission medium.

Another embodiment is depicted in FIG. 6. In FIG. 6 a defined passageway 86 passes through the catheter tip 50 and the catheter body 90. No internal seal exists between the catheter tip 50 and the catheter body 90, although a bulkhead may be provided that provides for fluid passage. The catheter body 90 and the catheter tip 50 may be filled with liquid fluid (not shown) from the proximal end 94 by adding such fluid into the defined passageway 86, such as from syringe 89 or other source. The defined passageway 86 extends to the catheter tip distal end 56. As needed depending on assembly practice, a fitting (not shown) may join sections of the defined passageway 86 at the joining end 54 where the catheter body 90 joins the catheter tip 50. By appropriate relative elevation positioning, air may escape through an opening (not shown) at or near the proximal end 94 while the fluid is filling. This approach avoids the need to have a sealable aperture, such as 39 in FIG. 5, in the catheter tip 50, and may not require interior components of the catheter body 90 or the catheter tip 50 to be biocompatible.

Figure 7:
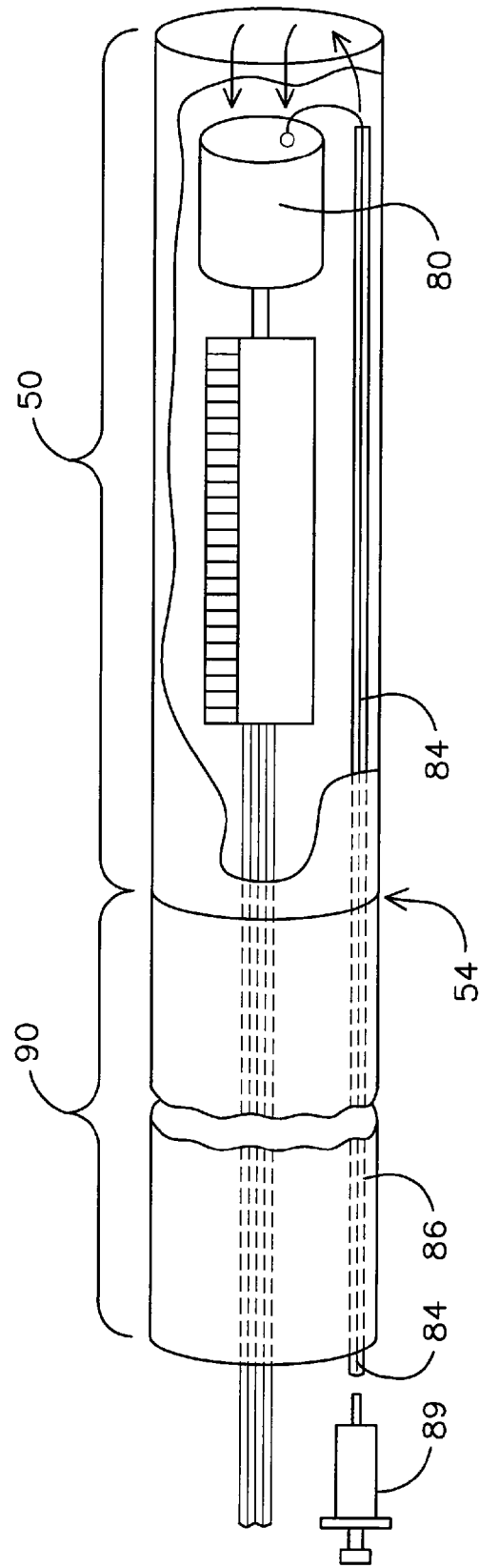
FIG. 7 is a side view with cut-away, partially internal view of an alternative exemplary embodiment of a catheter tip shown attached to a catheter body, similar to FIG. 6, which may be used in the imaging system of FIG. 1.

An embodiment similar to the embodiment depicted in FIG. 6 is depicted in FIG. 7. In FIG. 7, the defined passageway 86 additionally houses electrical conduits communicating with the actuator and/or transducer. These conduits, for the purpose of these examples, are referred to as the at least one conductive wire 84, which as described above connects the actuator 80 to an external rotary motor control (not shown).

An embodiment similar to the embodiment depicted in FIG. 7 is depicted in FIG. 8. In FIG. 8 the catheter body 90 additionally comprises a return passageway 98 extending from the catheter tip joining end 54 to an outlet (not shown) at the proximal end 94 of the catheter body 90. A seal 62 is provided to separate passage of fluid (not shown) in the catheter tip 50 so that the only passages into the defined space 70 are a defined passageway 96 (for inflow of fluid, and optionally provision of the at least one conductive wire 84 for the actuator 80) and the return passageway 98. Optionally, the passageways 96 and 98 may also be used to house steerable catheter deflection wires. For the embodiment of FIG. 8, it is appreciated that the return passageway 98 within the catheter body 90 may or may not also contain the interconnect wires 65 up to the joining end 54, where a bulkhead may or may not be utilized.

It is appreciated that for various embodiments, such as those depicted in FIGS. 3, 4, 7 and 8, the passage of a fluid may additionally provide a thermal management function. The operation of the actuators and transducers in catheter tips generates heat, and this heat may need to be distributed and dissipated in order to avoid undesired and/or disallowed heat build-up and transfer to a living tissue adjacent the catheter tip. The flow rate of open or closed fluid systems of the present embodiments may be regulated to maintain the temperature of the catheter tips to remain within a temperature range, or below a maximum allowed temperature. Various cooling devices may be added for open or for closed systems. Also, thermistor or other temperature sensing devices may be added to various regions or components of the catheter tips for establishment of warning and/or feedback control systems for thermal management.

FIG. 9 depicts an embodiment that comprises a seal 62, such as the seal 62 described for FIG. 4, however not necessarily comprising a seal aperture, such as 63, communicating with a defined passageway, such as 96. For this and other embodiments, the seal 62 may be in the form of a sealing bulkhead. However, the seal 62 in FIG. 9 comprises an opening 64 that communicates with a capillary-type reservoir 66 that is sealingly connected to the seal 62 and that extends proximally from the seal 62 into the catheter body 90 for a distance, ending with an opening 67. The defined space 70 and, optionally, a portion of the lumen of the reservoir 66, which is in fluid communication with the defined space 70, are filled with an acoustic transmission medium prior to operation. Then, when during operation the density of the acoustic transmission medium changes with changing temperature, a fluid boundary (not shown) in the capillary-type reservoir 66 will move to accommodate the change in density. During conditions of relatively high thermal expansion, fluid may expand to the point of filling the capillary-type reservoir 66 and may thereafter exit into the catheter body 90.

In other embodiments the reservoir 66 may comprise a flexible material adapted for expansion and contraction, so that the reservoir 66 provides a flexible space to accommodate changes in volume during changes in temperature of the acoustic transmission medium. Such temperature changes may occur during operation of the catheter tip 50 as the actuator 80 and/or the transducer array 60 generate heat. In such embodiments, the expansible volume of the reservoir 66 may prevent leakage from the catheter tip 50 that might otherwise result from pressure buildup, and may also prevent the incursion of air during a cooling down period.

FIG. 10 depicts an embodiment that does not utilize a fluid as the acoustic transmission medium between the transducer and the outer border of the catheter tip. In FIG. 10 a catheter tip 51 comprises a transducer array 60 that is encapsulated in a rotatable cylinder 55 comprised of a solid material that provides a desired ultrasound acoustical transmission. This solid material may be biocompatible and may be selected from polymers and silicones having an acoustic impedance between about 1.2 and 1.8 Mrayls. This is a non-exclusive listing.

As depicted in FIG. 10, transducer array 60 is a component of a transducer assembly 100, but this arrangement is not meant to be limiting. The rotatable cylinder 55 is positioned adjacent cut-out window 46 of an outer capsule 83 of catheter tip 51, and is in a driven relationship with an actuator 80. The conductive wire 84 connecting to actuator 80 may pass in a space between the rotatable cylinder 55 and the outer capsule 83 as is depicted in FIG. 10. Alternatively, conductive wire(s) to an actuator may pass through the rotatable cylinder 55 (not shown in FIG. 10, but see distal side of FIG. 11E) and may have sufficient additional length and flexibility adjacent the rotatable cylinder 55 to accommodate back and forth rotating motion. Also, albeit also not shown in FIG. 10, conductive wire(s) for actuators may pass through the rotatable cylinder and then become part of or adjacent to the interconnect (see proximal side of FIG. 11E).

As depicted in FIG. 10, interconnect 65 communicates with the transducer array 60 and is adapted to extend to or through a catheter body 90 adapted to receive the catheter tip 51. An outer, exposed portion of the cylinder 55 is in direct contact with blood tissue, or other material that is to be directly imaged. The inside surface of the catheter tip 51 that is adjacent the cylinder 55 may be lined with a lubricious material (for example, a polytetrafluoroethylene material), to allow cylinder 55 to rotate smoothly within catheter tip 51. The cylinder 55 may be manufactured to be in close tolerance to the catheter tip 51, and may act as a bearing. Alternatively, a moveable cylinder 55 may be achieved by other bearing relationships as known in the art. For example, not to be limiting, specific bearing surfaces may be provided in a full circle or in a partial arc along one or more sections of adjacent surfaces (which may allow gaps for passage of conductive wires, etc.), or such bearing surfaces may be segmented, or bearing surfaces may be provided at one or both of the proximal and distal ends of the cylinder 55, to bear against adjacent stationary surface(s) disposed in the catheter tip 51. Bearing surfaces and expected friction may be a function of the material selection (e.g., epoxy, metal, etc.), clearances, lubricity of materials or coatings thereon, and presence of a fluid there between.

FIG. 11A depicts another embodiment of an ultrasonic imaging catheter tip that may be adapted for connection to various catheter bodies. In FIG. 11A a catheter tip 53 comprises a transducer array 60 that is encapsulated in a rotatable cylinder 57. The rotatable cylinder 55 is positioned adjacent cut-out window 46 of an outer capsule 83 of catheter tip 53, and is in a driven relationship with actuator 80. Conductive wire 84 connects to actuator 80 as shown. Interconnect 65 communicates with the transducer array 60, shown as a component of transducer assembly 100, and is adapted to extend to or through a catheter body 90 adapted to receive the catheter tip. Seals, bulkheads, bearings and/or bushings, and drive linkages may be selected from those known to those skilled in the art.

The rotatable cylinder 57 is comprised of a solid material 72, such as a thermoplastic polymer, suitable for providing a desired structural integrity; it may or may not comprise a biocompatible surface. A fluid permeable membrane 69 is provided to cover window 46, and may be in direct contact with or may communicate with body tissue of the human or animal into which this catheter tip 53 is inserted for ultrasonic imaging. Accordingly, the fluid permeable membrane 69 is required to be biocompatible, and also is selected to provide an acceptable acoustic transmission. For some embodiments of a fluid permeable membrane such as 69, this membrane may be manufactured, packaged, shipped and stored in a dry state, and an appropriate fluid may be applied to this membrane prior to insertion into a body for use. Alternatively, upon insertion into a body for ultrasonic imaging, fluid uptake may occur into the membrane from adjacent body fluids. Alternatively, in other embodiments the membrane may be prepared in a moistened sterile state. Also, although depicted in FIG. 11A as only partially encircling the outer capsule 83, this is not meant to be limiting and a membrane may be provided that fully wraps around the outer capsule 83.

FIG. 11B provides a cross-sectional view of the embodiment of FIG. 11A taken along the B-B axis. This shows aspects of the arrangement of elements 60, 69, 72, 83 and 100, described above in FIG. 11A. The relative material thickness and dimensions for the fluid permeable membrane 69 shown in FIGS. 11A and 11B are not meant to be limiting.

Figure 11C:
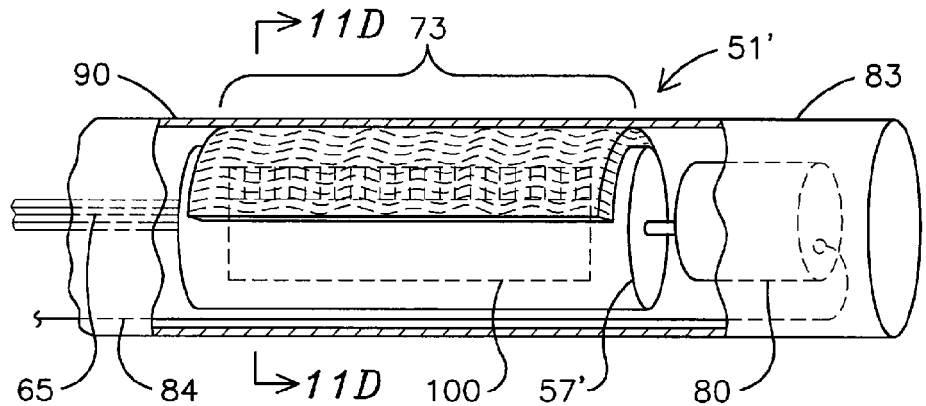
FIGS. 11C and 11D are, respectively, side with cut-away and cross-sectional views of another embodiment comprising a rotatable cylinder in a catheter tip.
Figure 11D:
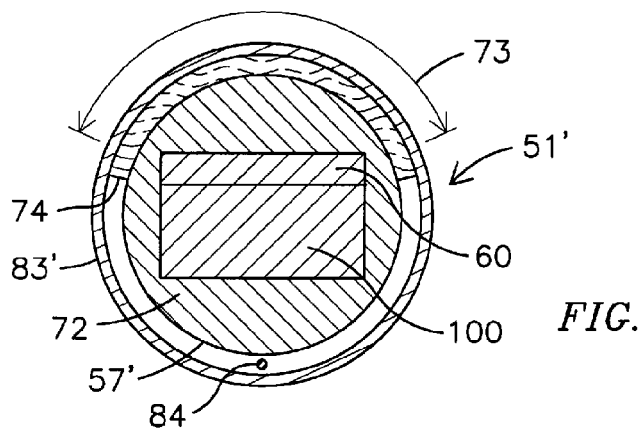

FIG. 11C provides a side, partial cut-away view of an embodiment of a catheter tip 51' comprising an outer capsule 83' comprising a window area 73 through which acoustical waves may travel from transducer 60 (depicted as a component of transducer assembly 100) embedded by a solid material 72 in rotatable cylinder 57'. Actuator 80 is in a driving relationship with rotatable cylinder 57', and conductive wire 84 connects to actuator 80 as shown. A gel layer 74 covers rotatable cylinder 57' at least in the area of window area 73. FIG. 11D provides a cross-sectional view of the embodiment of FIG. 11C taken along the D-D axis. As viewable in FIG. 11C and 11D, the gel layer 74 is between the transducer 60 and the interior surface of outer capsule 83' in window area 73 through which sound transmission occurs. The gel layer 74 may optionally surround the entire rotatable cylinder 57'. The approach depicted in FIGS. 11C and 11D provides an alternative to use of a fluid-filled catheter tip.

Figure 11E:
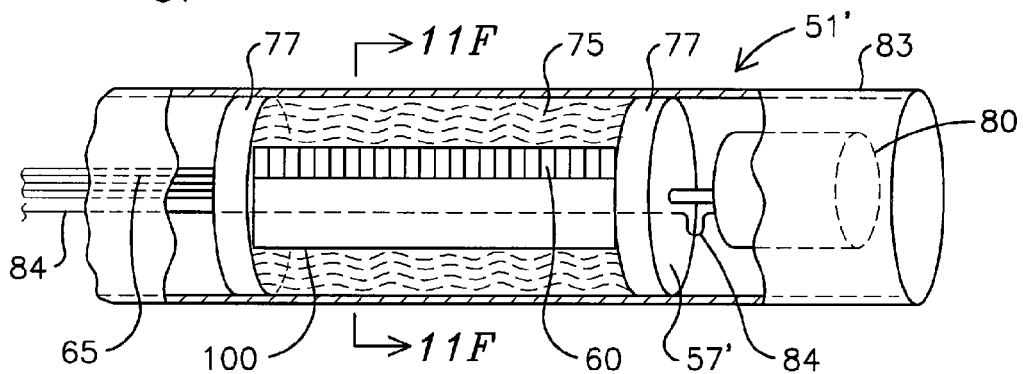
FIGS. 11E and 11F are, respectively, side with cut-away and cross-sectional views of another embodiment comprising a rotatable cylinder in a catheter tip.
Figure 11F:
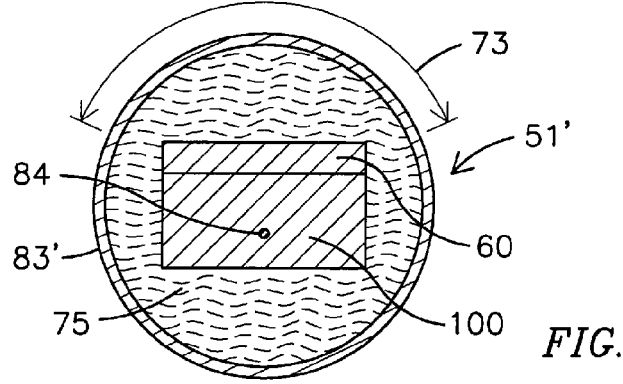

Alternatively, FIG. 11E provides a side, partial cut-away view of an embodiment of a catheter tip 51' in which a gel 75 fills a rotatable cylinder 57' that is defined at its proximal and distal ends by end structures 77 that may optionally have bearing and/or seal functions. Transducer 60, which is depicted as a component of transducer assembly 100, is positioned within rotatable cylinder 57'. Actuator 80 is in a driving relationship with rotatable cylinder 57', and conductive wire 84 connects to actuator 80 as shown. Acoustical waves (not shown) may travel through gel 75 between transducer 60 and window area 73 of outer capsule 83'. FIG. 11F provides a cross-sectional view of the embodiment of FIG. 11E taken along the F-F axis. This approach also provides an alternative to use of a fluid-filled catheter tip. It is noted that conductive wire 84 has a loop near actuator 80 to show a sufficient length to allow for rotational movement of the rotatable cylinder 57', passes through rotatable cylinder 57', and then passes alongside interconnect 65. This approach, however, is not meant to be limiting for arrangement of the conductive wire 84.

Figure 12A:
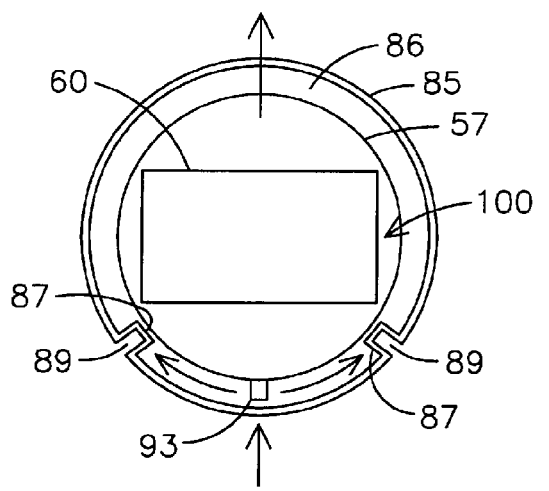
FIGS. 12A-C provide a specific alternative for alignment of a transducer to an acoustic window, such as may be utilized in embodiments such as those of FIGS. 11 and 12.
Figure 12B:
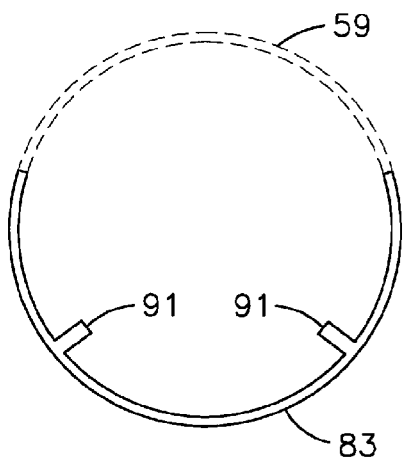
Figure 12C:
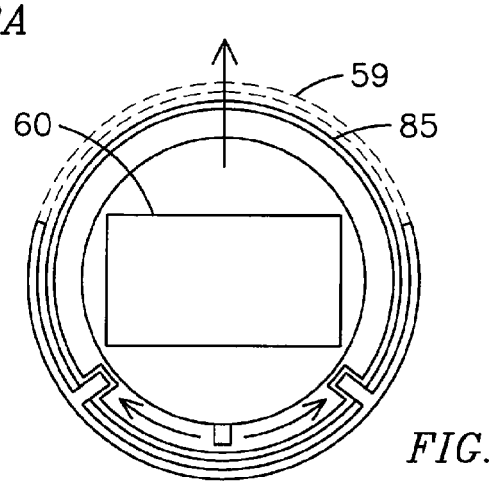

Further regarding embodiments comprising rotating cylinders such as those depicted in FIGS. 10 and 11, FIGS. 12A-12C provide one approach to aligning a transducer array 60 in a transducer assembly 100, which is embedded in a rotatable cylinder 57, to a window 59 (which comprises a cut-out section of an outer sheath or capsule 83). The rotatable cylinder 57 is housed in an inner sheath 85, with an acoustic transmission medium (not shown) in a space 86 between the outer border of the rotatable cylinder 57 and the inner sheath 85. The inner sheath 85 comprises two spaced apart hard stops 87, and a protrusion 93 on the rotatable cylinder 57 is between the two hard stops 87. The hard stops 87 have indentations 89, and are matched to keys 91 of the outer sheath 83. When assembled as shown in FIG. 12C, the inner sheath 85 is aligned with the outer sheath 83, and the transducer array 60 is aligned with the window 59. The particular mechanical features and arrangements are not meant to be limiting.

The above-described embodiments may comprise an outer cylindrical capsule comprised of a plastic that is resilient yet provides a limited flexibility, or may comprise an outer cylindrical capsule of other materials, such as described below. Generally, the hardness of various embodiments is such that the outer capsule (whether cylindrical or other cross-sectional shape), when a plastic, has an elastic modulus greater than about 0.5 and less than about 10.0 GPa. Plastics may include poly ether ether ketone [PEEK], polycarbonate, nylon, and polysulfone compositions.

Accordingly, in some embodiments ultrasound probe catheter tips may comprise a plastic outer cylindrical capsule within which are arranged a more distally positioned electromechanical actuator connected by a drive shaft to a more proximally positioned transducer array, which is connected to an interconnect adapted to communicate with a catheter system. Alternatives to such outer cylindrical capsule are provided in the following section, which also discloses methods of manufacture. Alternatives to such arrangement of components also are discussed herein.

It is appreciated that as used herein, the term "window" may be defined broadly as an area of a catheter tip through which the ultrasound passes, having appropriate impedance and other acoustic properties. As non-limiting examples, a window may comprise an actual cut-out section of a rigid outer capsule, such as a metallic capsule, or may comprise a region of a plastic outer capsule that has suitable properties as an acoustic transmission medium for the intended uses.

Figure 13:
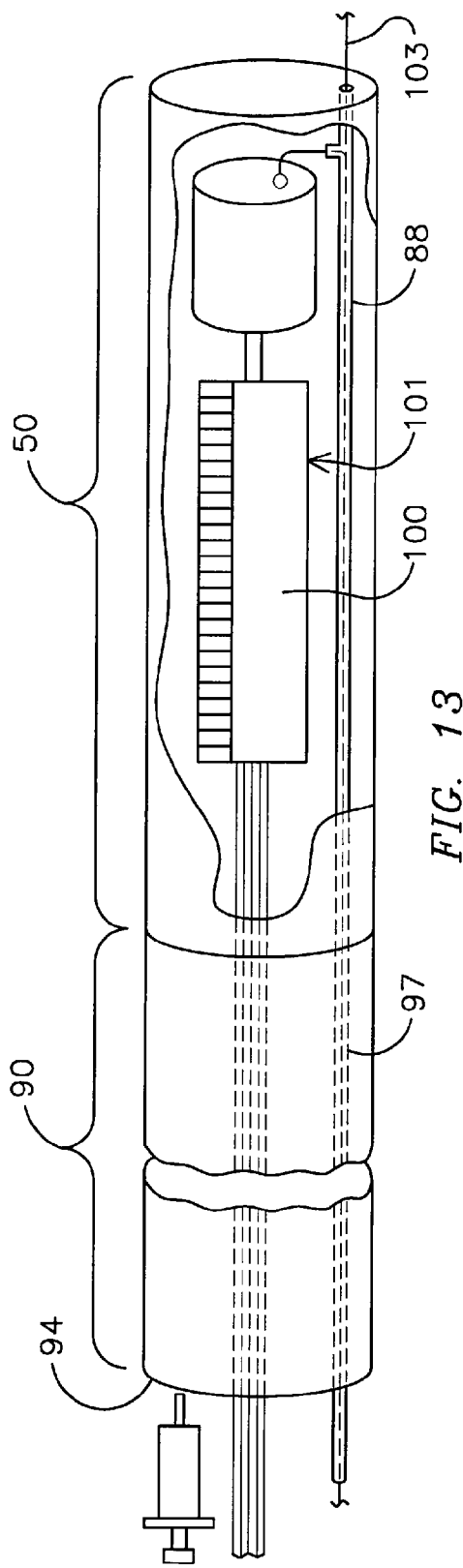
FIG. 13 depicts an optional conveyance passage that may be provided in various embodiments of the present invention.

Various of the herein-disclosed embodiments of catheter tips, and of catheter body/catheter tip combinations, may additionally comprise one or more longitudinal passages for receiving and guiding medical instrumentation, such as therapeutic and additional diagnostic devices, and/or for delivering treatments, such as medicines and stem cells. Exemplary medical instrumentation includes angiographic catheters, ablation catheters, cutting tools, blades and balloons. An example depicted in FIG. 13 depicts a conveyance passage 88 disposed in the defined space 70 between a back side 101 of transducer assembly 100 and the cylindrical outer capsule 52. This conveyance passage 88 is contiguous with or attachable to a confluent passage 97 in the catheter body 90, that extends to the proximal end 94 of the catheter body 90. This positioning leaves adequate space for back and forth rotational movement of the transducer assembly 100. A medical instrument, indicated by 103, may be inserted through confluent passage 97 and conveyance passage 88 to conduct a desired function outside of the catheter tip 50. The conveyance passage 88 also may be provided for over-the-guidewire techniques and systems, and may have its opening positioned so that the uses and/or effects of medical instrumentation may be observed by the ultrasonic imaging.

For the embodiments described above, various types of seals may be employed for the seal at the proximal end of the catheter tip. A structural type of seal is a bulkhead, which provides functional attributes as described herein. Also, for the embodiments described above, various types of bearings may also be provided. The seals and embodiments may include those described below.

As exemplified by various embodiments depicted and described herein, aspects of the invention also provide for manufacture of catheter tips that may be attachable to catheters of various designs from different manufacturers and then thereby suited for use in diagnostic imaging and/or therapeutic procedures. Catheter tips manufactured by methods disclosed herein may comprise a mechanically actuated rotatable transducer array that provides tilt scanning imaging, a mechanical actuator positioned in the tip for such actuation, and appropriate interconnects for attachment to a catheter. Alternatively, embodiments may provide at least one actuator coupled to a transducer array to provide other types of motion. A single actuator, or two or more actuators, may be provided in a catheter tip. For example, not to be limiting, two air bladder actuators, electroactive polymers, or multiple SMA wires, may be used in various embodiments that comprise more than one actuator. The embodiments described in parent application Ser. No. 11/289,926, filed Nov. 30, 2005 that comprise more than one actuator are specifically incorporated by reference for these examples and teachings, which include FIGS. 14-16 and the associated discussion. Arrangements also include the use of lead screw type piezo or electromagnetic actuators that create linear motion of the transducer. Also, voice coil type actuators could also be used to create linear oscillations or motion. In various embodiments disclosed below, approaches are provided for the fixed positioning of the actuator and transducer array with regard to an acoustic window. Also, in some embodiments a fluid filled reservoir is provided as part of a thermal diffusion system and for sound wave transmission fidelity within the tip. Catheter tips manufactured by the methods of the invention also are disclosed and claimed.

Generally, ultrasound image scanning for imaging other than a single two-dimensional image may fall into three categories: linear scanning; tilt scanning; and rotational scanning. As one example, a tilt-scanning real time three dimensional imaging may comprise a transducer that sweeps back and forth along a defined arc to include a desired volume of adjacent tissue. This sweeping is about an axis defined by the centerline of the catheter tip section in which the probe is housed. The transducer obtains a number of two-dimensional images during the sweeping cycle and these images may be combined to generate a three-dimensional image. Repeating this sweeping at specified time intervals may provide real time imaging of the tissue, and this may allow for real time visualization of anatomical processes as well as observation of interventional procedures, including procedures effectuated from the same catheter that houses the ultrasound probe.

Such real time three dimensional imaging may find particular use in intracardiac echocardiography (ICE) as well as other diagnostic and interventional fields. Reliable, cost-effective real time three dimensional imaging with a catheter-based ultrasound probe requires the provision of catheters that comprise an appropriately sized transducer array that is moveable (i.e. rotatable for tilting or rotational scanning).

Figure 14A:
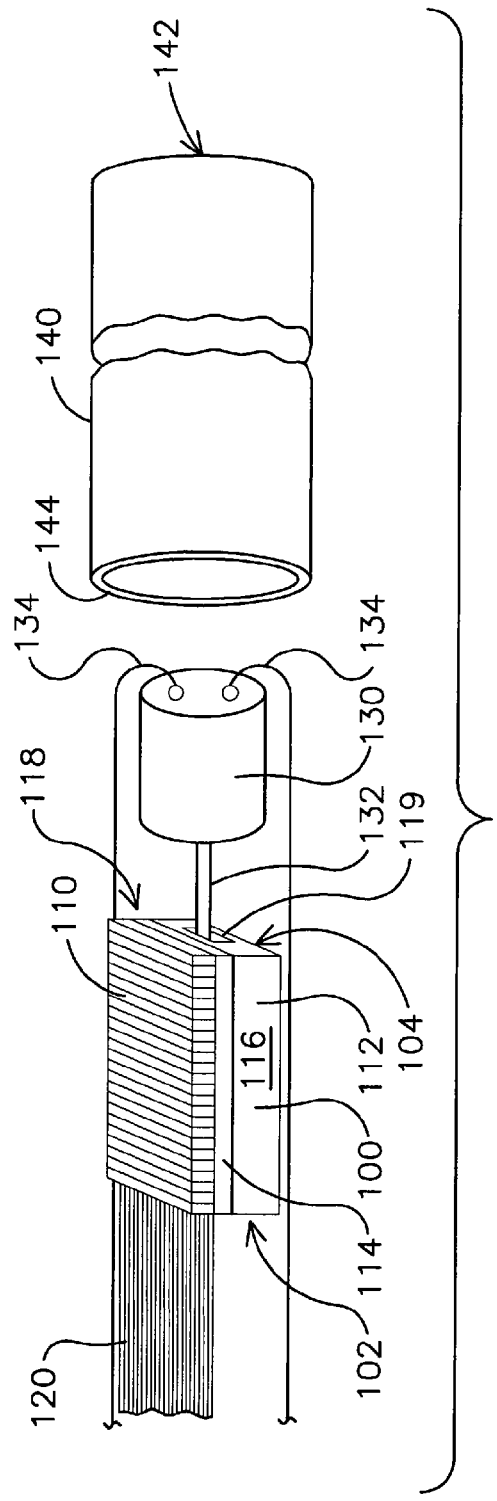

FIGS. 14A-H exemplify steps of one embodiment of manufacture of catheter tips that may find particular use in ICE and other diagnostic and interventional fields. FIG. 14A depicts an ultrasound transducer assembly 100 having a proximal end 102 and a distal end 104, where the proximal end 102 is closer to a connection to a catheter (not shown), and to the proximal end of the catheter that lies outside a body being examined during operation (also not shown). The ultrasound transducer assembly 100 comprises a transducer array 110. This may be a phased array, which may include a flat phased array a curved array, or a phased sector array, or other types of arrays as is appropriate for the application, such as, but not limited to, a linear sequential array, a multi-row array, and other 1D and 2D arrays. As depicted in FIG. 14A, but not meant to be limiting, ultrasound transducer assembly 100 also comprises a backing layer 112 to dampen and thereby shorten pulse duration, and an electrical connection layer 114. The electrical connection layer 114 provides electrical communication between electrical conduits passing to transducers in the transducer array 110 and an interconnect 120 that communicates through a catheter channel (not shown) to an ultrasound control system (not shown), where electrical signals are generated to produce ultrasound signals and where ultrasound data is collected and analyzed. While depicted in FIG. 14A as a thin layer between the transducer array 110 and the backing layer 112, this is not meant to be limiting. Electrical leads for the transducer array 110 may pass along edges 116 and/or 118 of the transducer array 110 to electrical connections (not shown) that would comprise the electrical connection layer 114 along the respective sides of the ultrasound transducer assembly 100. More generally, the electrical connection layer 114 and/or the interconnect 120 may comprise a printed circuit board (PCB), such as a flexible PCB, and the electrical connection layer 114 may be positionally distinguishable from but structurally identical with the interconnect 120. Also, a variety of connection devices (not shown) may be used to operatively connect the interconnect at points between the ultrasound transducer assembly and the ultrasound control system, to allow signals to be transmitted and/or received. Such connection devices include but are not limited to spring or wire contacts, tabs, plugs and other configurations known to those skilled in the electrical interfacing and wiring fields, and optical and/or electromagnetic connections.

Considering the above-described example as non-limiting, one step is providing an ultrasound transducer assembly adapted for use with a catheter, the ultrasound transducer assembly comprising a proximal end and a distal end, a drive linkage to an actuator at the distal end, and a transducer array, where the transducer array is electrically connected to an interconnect adapted for passage to or through the catheter.

In another step, an example of which is depicted in FIG. 14A, the ultrasound transducer assembly 100 connects to an electromechanical actuator 130 for mechanical rotation. As depicted in FIG. 14A, to achieve this connecting the ultrasound transducer assembly 100 comprises a coupling, or drive linkage 119, to receive a drive shaft 132 of the electromechanical actuator 130. In FIG. 14A the drive linkage 119 is depicted as a slotted orifice within the body of the ultrasound transducer assembly 100 at its distal end 104. The drive shaft 132 comprises a mating flattened end for insertion into the drive linkage 119 to effectuate a positive mechanical drive connection. This is not meant to be limiting, and any drive linkage known to those skilled in the art may be utilized to drivingly connect the electromechanical actuator 130 with the ultrasound transducer assembly 100 to achieve a solid mechanical drive connection for actuation, which may include an adhesive mating of components. Electrical conduits, such as conductive wires 134, pass from the electromechanical actuator 130 to a controller (not shown) of the ultrasound control system so as to provide, during operation, electrical energy to rotate the drive shaft 132 in a desired pattern to effectuate a desired scanning (i.e., tilt scanning) of the ultrasound transducer assembly 100. The electrical conduits need not comprise the conductive wires 134 as depicted in FIG. 14A, and may be consolidated into the interconnect 120 for simpler passage through the catheter (not shown).

As depicted in FIGS. 14A and 14B, another step comprises inserting the ultrasound transducer assembly 100 and the mechanical actuator 130 into an acoustically transparent sheath 140 comprising a closed end 142 at its distal end and an open end 144 at its proximal end. When so inserted, a defined space 146 remains that is to be filled with an acoustic transmission medium as is discussed below in another step.

As depicted in FIGS. 14C and 14D, another step comprises inserting the sheath 140 into a rigid capsule 150 that comprises a cylindrical body 152, an open proximal end 154 adapted for connecting to a catheter, and an acoustic window 156 along the cylindrical body 152. It is noted that the body 152 need not be cylindrical, but may be of any cross-sectional configuration providing a hollow space therein suitable for insertion and desired motion of a transducer. In various embodiments, the acoustic window 156 comprises an opened section of the cylindrical body 152 formed by removal of material. Such acoustic windows may be formed by laser processes, by mechanical machining, or by casting or other processes known to those skilled in the art. A window so formed may remain open as depicted, or may be covered in an additional optional step (not provided in figures) of adding a window cover. Such optional window cover may provide additional structure and/or protection of an inner sheath such as sheath 140. Candidate materials having suitable low-attenuation, which may be used for such window covers (and for entire plastic outer capsules as described elsewhere) may include, but are not limited to, polyethylene, silicone rubber, polyvinyl chloride, polyurethanes, polyesters, natural rubbers, polymethylpentone, polyimide, polyether ether ketone, nylon, polysulfone, and polycarbonate As used herein, the term "rigid" as applied to a capsule, such as capsule 150, means that the structure of the capsule is sufficient to support stresses placed upon it during a normal range of uses without deforming. More particularly, a rigid capsule may be constructed of materials that include, but are not limited to, stainless steel, cobalt alloys, reinforced polymers, copper, silver, aluminum, brass, and titanium, and the rigid capsule so constructed may have a modulus of elasticity between about 20 and 500 GPa, and more particularly, between about 40 and 250 GPa, and more particularly, between about 100 and 245 GPa, and all subranges there between. Constructing the capsule 150 in some embodiments may include selecting materials and designs that facilitate thermal management of the electromechanical actuator 130 as well as that provide shielding of electromagnetic interference.

The acoustic window 156 provides a region through which ultrasound waves may pass (from and back to the transducer array 110) without undesired loss or modulation of signal. The step comprising inserting the sheath 140 into the rigid capsule 150 may inherently include proper alignment of the transducer array 110 to the acoustic window of the rigid capsule 150. This alignment may be achieved by initial orientation prior to the inserting, and the frictional pressure of a tight fit of the sheath 140 against the rigid capsule 150 may provide a non-moving secure positioning of such alignment. Other mechanical engagements, as are known to those skilled in the art may be employed.

Figure 14E:
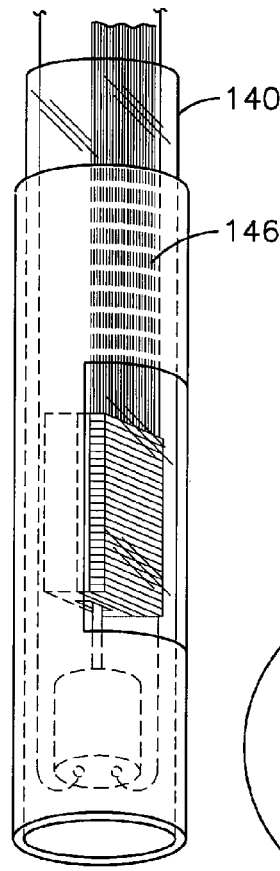

Alternatively, when such alignment does not occur concomitantly with the inserting step, an optional step is aligning the transducer array 100 to a desired position in relation to the acoustic window 156 for transmission of acoustic waves through the acoustic window 156. An optional sub-step of this step is securing this position to retain this aligning throughout the operational life of the catheter tip. FIG. 14E depicts the ultrasonic array 100 positioned so the transducer array 110 is aligned to a proper, desired orientation to the acoustic window 156. Alternatively, a final alignment of the transducer array 110 to the window 156 (such as after a first alignment of the interconnect 120 in relation to the window 156) may be by calibrating rotational movement of the actuator to achieve an oscillation of the transducer array 110 that is centered in relation to the window 156.

Figure 14F:
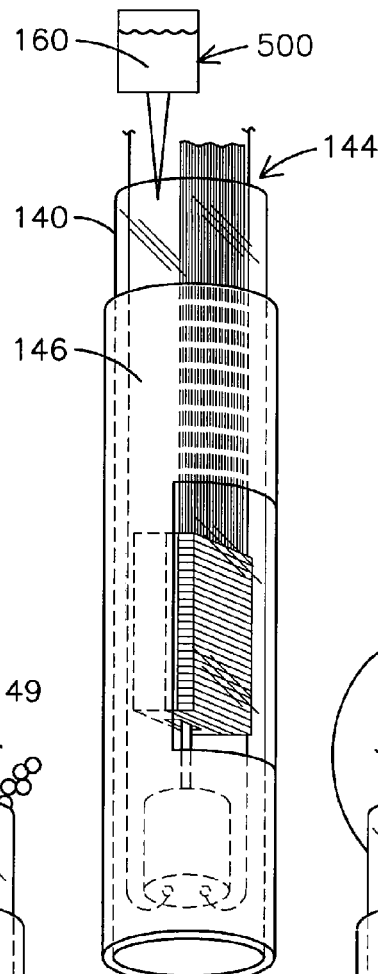

As noted above, the space 146 in sheath 140 is to be filled with acoustic transmission medium. For example, as depicted in FIG. 14F, the capsule 150 containing the sheath 140 and components therein is disposed vertically with the open end 144 oriented upward. A dispenser 500 provides a volume of acoustic transmission medium 160 to fill the sheath 140 to a determined level. This accomplishes the step of filling the sheath with an acoustic transmission medium.

Figure 14G:
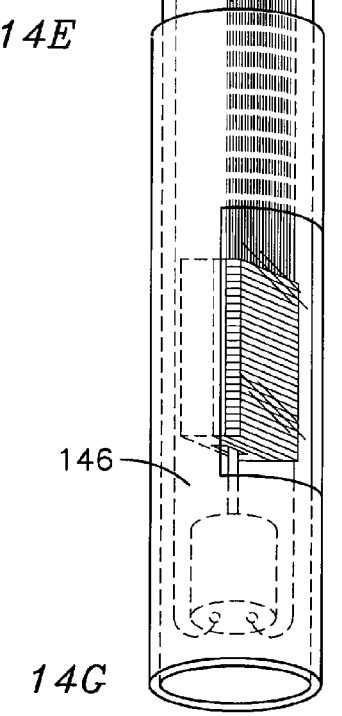
Figure 14H:
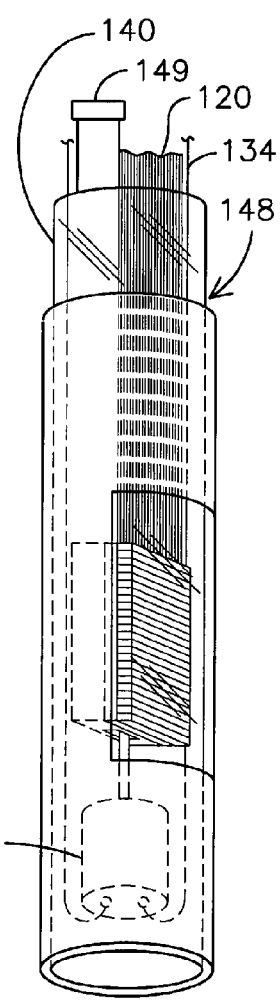

Another step is degassing the acoustic transmission medium 160. As depicted in FIG. 14G, this is done while the acoustic transmission medium 160 resides in the sheath 140. This may be achieved by any approach known to those skilled in the art, such as by applying a vacuum to the immediate physical environment of the sheath 140 containing the acoustic transmission medium 160. However, the step of degassing the acoustic transmission medium may be done in any other manner, and may include degassing a quantity of acoustic transmission medium prior to dispensing into one or more sheaths (such as sheath 140), and then adding to such sheaths with minimum handling and/or under partial vacuum, with optional vibration and/or repositioning to remove air that may be entrapped in spaces within the catheter tip. Another step is sealing the sheath 140 at a sealing location 148 more proximal than the proximal end 102 of the ultrasound transducer assembly 100. This sealing, such as is depicted in FIG. 14H, provides for the interconnect 120 to pass proximal from the point of sealing either for connection to a second interconnect that passes through the conduit, or for passing entirely through the conduit and connecting to a connection of the ultrasound control system (not shown). Similarly, the conductive wires 134 connecting to the electromechanical actuator 130 need to pass through the sealing location 148 for passage to or through the catheter (not shown). Sealing location 149 may be sealed at this time to seal the proximal end of an optional reservoir, discussed elsewhere herein.

The assemblage of components so fabricated is identified as catheter tip 170 in FIG. 14J. This may be connected to a catheter 300 at a distal end 302 of the catheter 300. A quantity of catheter tips such as catheter tip 170 may be mass produced in one location, and then shipped to various manufacturers of catheters, or to medical centers, for assembly. Catheter tips may be provided with different interconnects and other features, such as designs for connection, to mate with the catheters of different manufacturers.

Further, and referring more specifically to FIG. 14J, the length of interconnect 120 outside the catheter tip 170 may be sufficiently long to pass entirely through a catheter body, such as catheter body 300, or may be short and end with a connection mating to a an end of a second interconnect at or near a distal end 302 of catheter body 300. In FIG. 14J, a free end 121 of interconnect 120 extends through a proximal end 304 of the catheter body 300 (and may thereafter connect with an ultrasound control system, not shown). As noted elsewhere, conductors 134 for the actuator (not shown) may be consolidated into the interconnect 120 or may be passed through the catheter body 300 separately. An assembled view, and an enlarged view of a lap connection between the catheter tip 170 and distal end 302 are provided in FIG. 14K. The lap joint at the capsule proximal end 154 may be tapered to provide a snug fit, and an adhesive may be used to bond the lap joint surfaces together. Alternatively, a lap or other type of joint may be thermally or chemically welded.

Figure 14L:
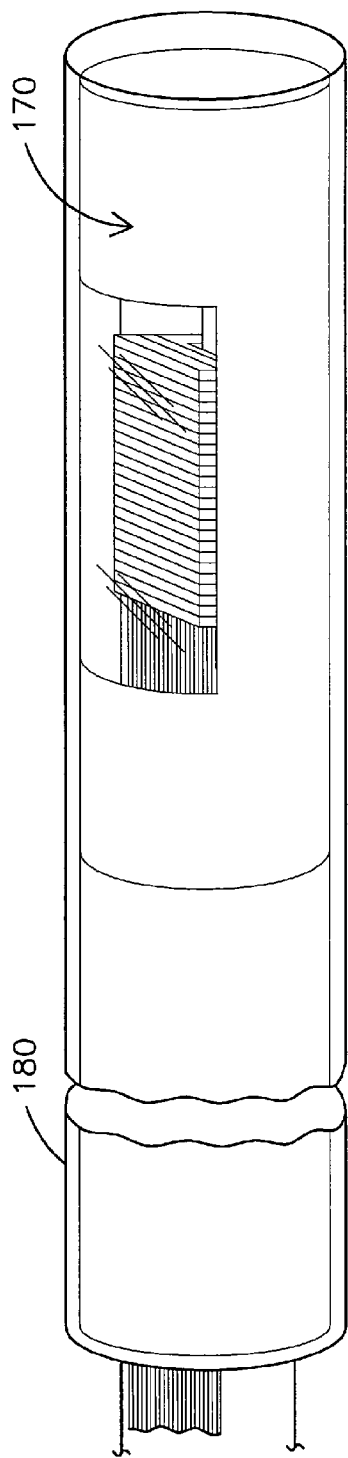

An optional step in final assembly of a catheter to a catheter tip as fabricated herein is applying a thin coating 180 over the catheter tip and at least a distal portion of the catheter, as depicted in FIG. 14L. This covers and seals all surfaces and joints of the catheter tip 170.

It is appreciated that the steps exemplified in FIGS. 14J to 14L are not meant to be limited to catheter tips manufactured by the methods described corresponding to FIGS. 14A through 14H. Rather, the assembly method of a catheter tip to a catheter body, such as depicted in those figures, may be applied for any catheter tip of the present invention, and may generally be described as follows:

a. assembling a catheter tip comprising a distal end, a proximal end, and an interconnect of a length sufficient to pass through a specified catheter body;
b. passing a free end of the interconnect through the specified catheter body; and
c. attaching the catheter tip proximal end to the catheter body.

This method may be applied to a catheter tip for any type of diagnostic and/or interventional catheters known in the art, including catheters having ablation and recanalization functionalities (e.g., balloon angioplasty, laser ablation angioplasty, balloon embolectomy, aspiration embolectomy, heat probe ablation, abrasion, and drilling). More particularly, the catheter tip may be an ultrasonic imaging catheter tip as disclosed elsewhere herein, and may comprise an actuator, such as an electromechanical actuator, to drive a moveable transducer or transducer array. In various embodiments, the interconnect is flexible or comprises a flexible region to allow a desired reduced torque for rotation during movement of the actuated transducer or transducer array. This reduces the torque requirements for the actuator. Thus, in various embodiments the interconnect comprises a rotatable aspect. An additional optional step is to apply an outer protective coating or layer as is exemplified in FIG. 14L.

Generally speaking, proper alignment of the actuator, drive shaft, transducer array, acoustic window and interconnect helps ensure accurate image acquisition. In the above example, the step of aligning the transducer array 100 to a desired position in relation to the acoustic window 156 was discussed. A sub-step of this step is securing this position to retain this aligning throughout the operational life of the catheter tip. The step of aligning, including the sub-step of securing, may be implemented a number of ways such as by providing mechanical supports in certain components and establishing appropriate connections from such mechanical supports to adjacent structures to secure the alignment.

Figure 15A:
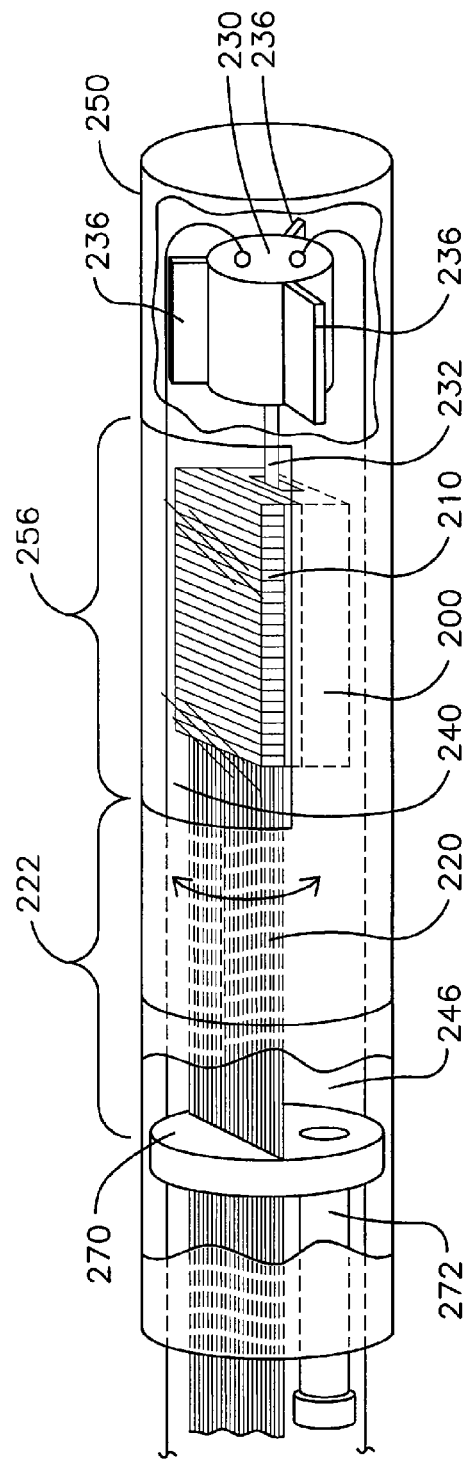

A non-limiting specific embodiment of providing mechanical supports and establishing connection to adjacent structure is depicted in FIG. 15A. Three motor mounts 236 extend radially from electromechanical actuator 230. Also, a bulkhead 270 is positioned proximal to ultrasound transducer assembly 200 comprising a transducer array 210. With the drive shaft 232 of electromechanical actuator 230 connected to ultrasound transducer assembly 200, the electromechanical actuator 230 is aligned to a desired position relative to an acoustic window 256. Also, the bulkhead 270 is aligned to provide a desired length 222 of interconnect 220 between itself and the ultrasound transducer assembly 200 to provide for non-restricted, or for reduced torque load rotational movement during operation, and the interconnect 220 may be positioned in relationship to the window 256 so that the interconnect 220 flexes about equally as the ultrasound transducer assembly 200 would move to both sides of a midline of the window 256. Then the motor mounts 236 are secured to or through the sheath 240 to the rigid capsule 250, and the bulkhead 270 is secured to or through the sheath 240 to the rigid capsule 250. One approach to such attaching, or stably affixing, is by crimping the capsule 250 into motor mount 236 at one or more points of the motor mounts 236.

Thus, a fabrication step that utilizes a bulkhead such as exemplified by bulkhead 270 may be described as sealing the sheath by inserting and securing a bulkhead at a point more proximal than the proximal end of the ultrasound transducer assembly, however providing for the interconnect to pass through the bulkhead and proximal from the point. It is understood that a step of aligning the bulkhead also may be performed, such as to provide a desired rotationally uniform positioning of the length 222 of interconnect 220 to assure non-binding rotation in both angular directions (shown by arrows) as the ultrasound transducer array 200 moves during operation.

The alignment also may be achieved, wholly or in part, by electronic alignment of the actuator 230, to control the angular range of motion to coincide and/or be centered in the window. This may be achieved since the drive shaft is rotatable with respect to the actuator (and hence the motor mount). Also, generally, the motor mounts may engage spaced apart slots in the rigid capsule that provide for an alignment and/or more general positioning function.

FIG. 15A also depicts an optional flexible fluid reservoir 272 in fluid communication with the defined space 246 formed within the acoustically transparent sheath 240. This fluid reservoir 272 is positioned outside the defined space 246, is flexible, and functions during operation to maintain the fluid-filled defined space 246 within rigid capsule 250, accommodating fluid volume changes with temperature changes, and to provide additional volume for fluid. The flexible fluid reservoir 272 comprises flexible, bladder-like walls that have sufficient flexibility to respond to such volume changes without substantial pressure changes occurring in the space 246. For example, silicone tubing or urethane composites may comprise the flexible fluid reservoir 272. The flexible fluid reservoir 272 thereby is effective to expand and contract during operation to maintain a temperature-equilibrated fluid volume in the sheath 240. A capillary-type reservoir, as disclosed above, alternatively may be employed to accommodate fluid volume changes to maintain the defined space 246 in a fluid-filled condition. Such capillary-type reservoir may not expand and contract, but rather fluid would occupy varying portions of the reservoir during different thermal states.

In an alternative embodiment, a fluid reservoir (such as in FIG. 15A, however more centrally disposed) may enclose an interconnect, such as interconnect 220 in FIG. 15A, to a point proximal where the interconnect may be exposed for connection and/or may be sealingly passed through a proximal end wall of the fluid reservoir, and thereby into the space of a catheter body.

Accordingly, embodiments of methods to fabricate a catheter tip encapsulating a mechanically actuated ultrasound transducer assembly generally may comprise providing a flexible fluid reservoir in fluid communication with the acoustic transmission medium in the sheath and extending externally to the sheath, filling the flexible fluid reservoir with the acoustic transmission medium, and sealing the flexible fluid reservoir to maintain its fluid communication with the acoustic transmission medium in the sheath. When the fluid reservoir is affixed to a bulkhead such as component 270 described above, embodiments of such methods may more specifically comprise a step of affixing an open end of a flexible fluid reservoir to a bulkhead, and sealing the sheath by inserting and securing a bulkhead at a point more proximal than the proximal end of the ultrasound transducer assembly, however providing for the interconnect to pass through the bulkhead and proximal from the point.

Figure 15D:
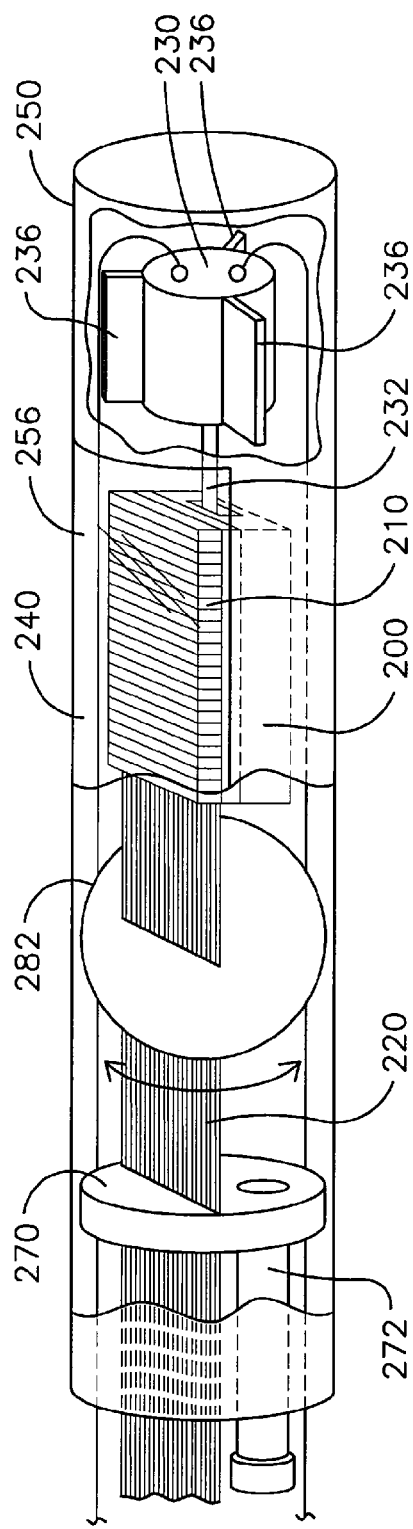

Other specific embodiments involve providing additional mechanical supports to adjacent structure and are depicted in FIGS. 15B through 15D. In addition to three motor mounts 236 that extend radially from electromechanical actuator 230, and bulkhead 270, in FIG. 15B a cylindrical rotating bearing 280 is positioned between the ultrasound transducer assembly 200 and the bulkhead 270. The interconnect 220 passes through a central region of the bearing 280, and movement of the interconnect 220, due to actuation of the transducer assembly 200 by the actuator 230, causes movement of the bearing 280. A relatively broad cylindrical surface 281 of the rotating bearing 280 has a bearing relationship with the opposing and adjacent acoustically transparent sheath 240. This is effective to provide a desired level of force distribution against the sheath 240, and during operational movement of the ultrasound transducer assembly 200 the rotating bearing 280 will rotate (see arrows), being driven by motion transferred through the interconnect 220. In an alternative embodiment, a rotating bearing may not be attached as shown to the interconnect 220, and rather may be attached to the proximal end 202 of the ultrasound transducer assembly and function to stabilize that proximal end 202 during operational movements. To illustrate this, in FIG. 15C a cylindrical rotating bearing 280' is attached to the proximal end 202 of ultrasound transducer assembly 200.

It also is noted that a rotating bearing may be spherical instead of cylindrical, as is depicted with a spherical bearing 282 in FIG. 15D. This bearing 282 comprises a relatively narrow region of contact with the sheath 240, and the interconnect 220 passes through it. In various embodiments the section of interconnect 220 between the respective bearings 280, 280', or 282 and the seal 270 is sufficiently flexible to provide a reduced torque during movement. The steps as described herein, and in the claims, need not be conducted in the sequence shown. As but one example of a different sequence of steps, a sheath may be inserted into a capsule prior to inserting a transducer assembly and electromechanical actuator into the sheath. Also, aligning may occur between any of a number of other steps in accordance with appropriate manufacturing line practices. Quality control and quality assurance procedures may be introduced as needed into the various embodiments of methods to fabricate catheter tips as disclosed and claimed herein.

Likewise, the arrangement of components is not meant to be limiting. One alternative arrangement is depicted schematically in FIG. 16, in which a catheter tip 170 having a proximal open end 304 (for attachment to a catheter body, not shown) and a closed distal end 302 comprises a more proximal actuator 80 connected to a more distal transducer array 210. An interconnect 220 extends distally to a cylindrical rotating bearing 280, which comprises a gap (not shown) for passage of the interconnect 220 back to the proximal end 304 after making a loop at the distal end 302.

FIG. 17A, a side view with cut-away, partially internal view, and FIG. 17B, a cross-section view taken at line B-B of FIG. 17A, present an additional exemplary embodiment. In this particular embodiment a catheter tip 750 defined exteriorly by an outer capsule 752 comprises a transducer assembly 700 having a transducer array 710 embedded in a potting material formed into a body 711 that is rotatable within the catheter tip 750, where the potting material body 711 is surrounded in the catheter tip with an acoustic transmission medium 760. In FIGS. 17A and 17B, the shape of the body 711 is a cylinder 755, which is sized so as to rotate smoothly within the cylindrical contour of the outer capsule 752 of the catheter tip 750. However, this cylindrical shape is not meant to be limiting, and variations in shape from a cylinder are within the scope of the invention. As one example, not to be limiting, the shape of a potting material body in a particular embodiment may be a partial cylinder, covering only the topside of the transducer, where such shaped potting material body is rotatable within a respective catheter tip. To exemplify this, FIG. 17A has a contour line 777 below which, in variations of what is depicted in FIG. 17A, the potting material body is reduced or eliminated, and thus does not conform to the cylindrical profile above the dashed line 777. Further, one skilled in the art will appreciate that the shape of the potting body need not be of a cylindrical shape, since other geometric shapes may be readily utilizable in alternative embodiments of the present invention.

In the particular embodiment depicted in FIGS. 17A and 17B, a catheter body 790 joins the catheter tip 750 at a joining end 754 that is occupied with a bulkhead 748. An interconnect 720 passes through the catheter body 790 and bulkhead 748 to connect to the transducer assembly 700 comprising the transducer array 710. An actuator 730 is disposed at a distal end of catheter tip 750 relative to the cylindrically shaped potting body 711 housing the transducer assembly 700. The actuator 730 is attached by a drive shaft 732 to drive the cylinder-shaped potting material body 711, so as to move the transducer assembly 700 in, for example, a reciprocating motion having a desired rotation angle range of motion. The drive shaft 732 selectively may attach to the potting material body 711 itself or to the transducer assembly 700, such as with a specific drive linkage (not shown). A motor interconnect 735, such as one or more conductive wires, supplies power and control signals to the actuator 730.

In the particular embodiment depicted in FIGS. 17A and 17B, a defined space 746 not otherwise filled with components is filled with acoustic transmission medium 760. This acoustic transmission medium may be of a low viscosity, about the viscosity of water, and would occupy the relatively thin defined annular space 761 between a cylindrical outer surface 712 of the cylinder-shaped potting material body 711 and an inner surface 751 of the catheter tip 750 (here, specifically, of the outer capsule 752 (see FIG. 17B)). An acoustic transmission medium, which may alternatively be considered to be an acoustic coupling fluid, may have a viscosity of between about 1-20 cP.

In such embodiment, the material generally comprising catheter tip 750, or specifically overlying the area through which ultrasound signals pass from and to the transducer assembly 700 (which is recognized as a window or window area, shown generally as 756) may be selected from materials providing low levels of interference and low loss of acoustical energy. In various embodiments the potting material body 711 may have an acoustic impedance between about 1.2 and 1.8 Mrayls. In various embodiments the potting material body 711 may be biocompatible and may be selected from polymers and silicones. This is a non-exclusive listing; other materials may be non-biocompatible. Further specific examples of acoustically neutral materials include polyether block amide (PEBAX), polyurethanes (PU), and polymethylpentene (TPX). It is noted that the use of an appropriately shaped potting material body 711 housing the transducer assembly 700, such as the cylinder in this example, allows for the window or window area 756 or the entire catheter tip 750 to be made of a relatively more flexible material, such as TPX tubing, as the rigidity provided by the cylindrical potting material body 711 functionally supports the adjacent window or window area 756. In addition, to reduce friction between the cylindrical potting material body 711 and the inner surface 751 of catheter tip 750, one or more of the cylindrical outer surface 712 of the cylinder-shaped potting material body 711, the inner surface 751 of catheter tip 750, and the acoustical coupling fluid 760 have a lubricious property.

Figure 16:
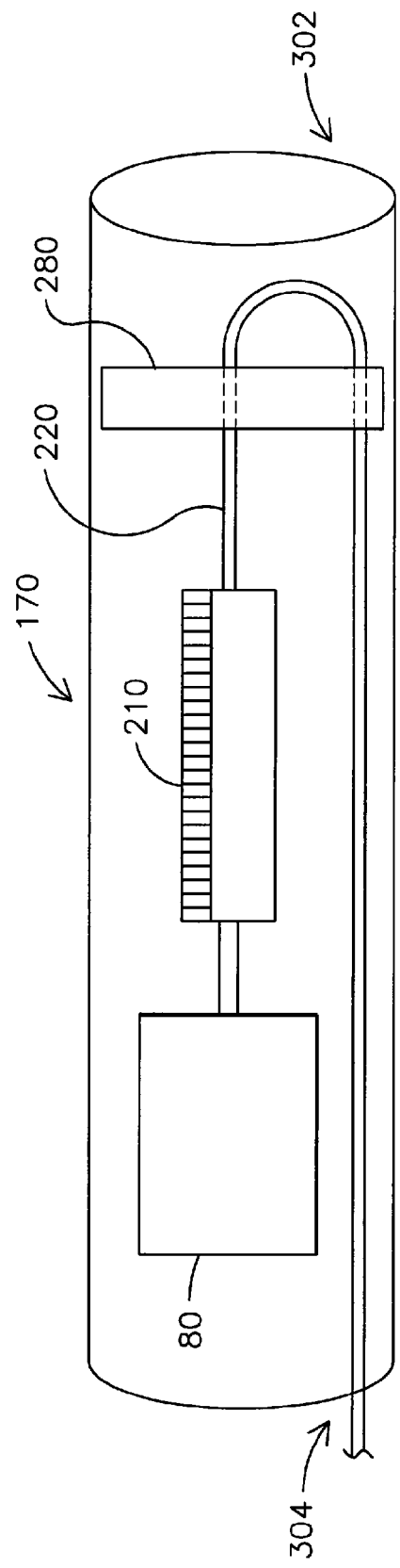
FIG. 16 is a side and internal view of an alternative exemplary embodiment of a catheter tip providing an alternative arrangement of components therein.
Figure 17C:
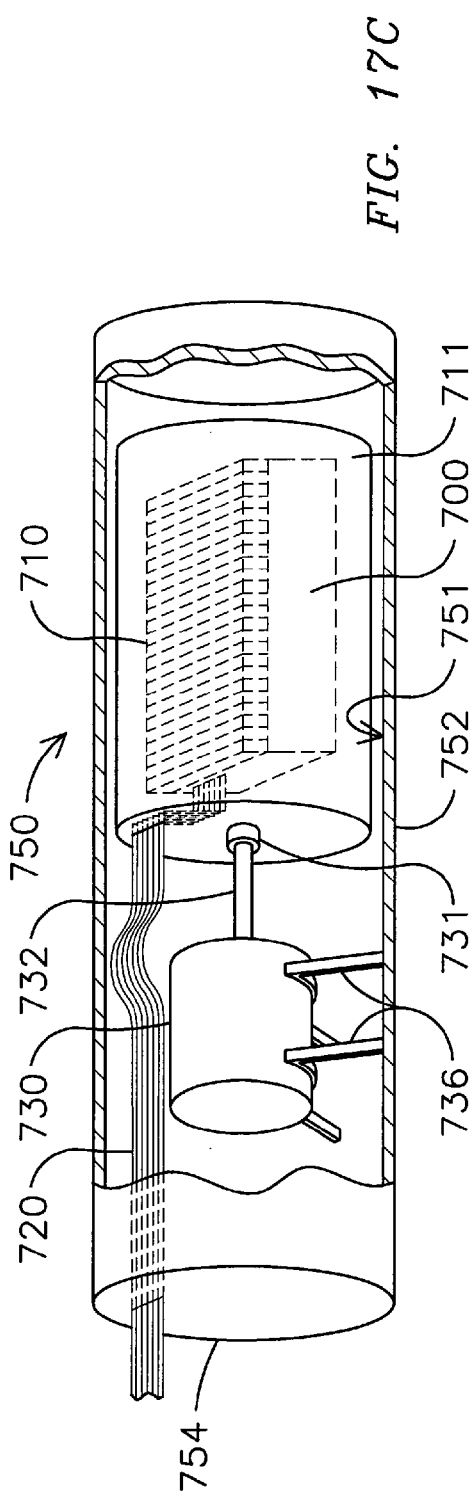
FIG. 17C is a side biew with cut-away of an alternative embodiment with a more proximally disposed actuator.

FIG. 17C provides a side view with cut-away of an alternative embodiment, not meant to be limiting, of a catheter tip 750 in which an actuator 730 is more proximal joining end 754 than a more distally positioned potting material body 711 comprising a transducer array 710 (which selectively may or may not be provided within a transducer assembly 700). The actuator 730 as depicted is supported by optional motor mounts 736 and is sized so as to provide sufficient space for an interconnect 720, which connects to the potting material body 711 as shown in the figure. The actuator 730, which may be electromechanical, is connected to or comprises a drive shaft 732 in a torque transmitting relationship with a coupling 731 of the potting material body 711. Although not specifically shown, a drive shaft such as drive shaft 732 may alternatively be in a torque transmitting relationship with a coupling of a transducer assembly such as transducer assembly 700. The potting material body 711 may bear against the inner surface 751 of the catheter tip 750's outer capsule 752, or may optionally or additionally be in a rotationally supportive relationship with a more distally disposed bearing or bushing (not shown in FIG. 17C). It also is appreciated that an arrangement of components such as shown in FIG. 16 may be utilized in various embodiments, however wherein there is a rotatable potting body enclosing the transducer array (such as array 210 in FIG. 16).

Figure 18:
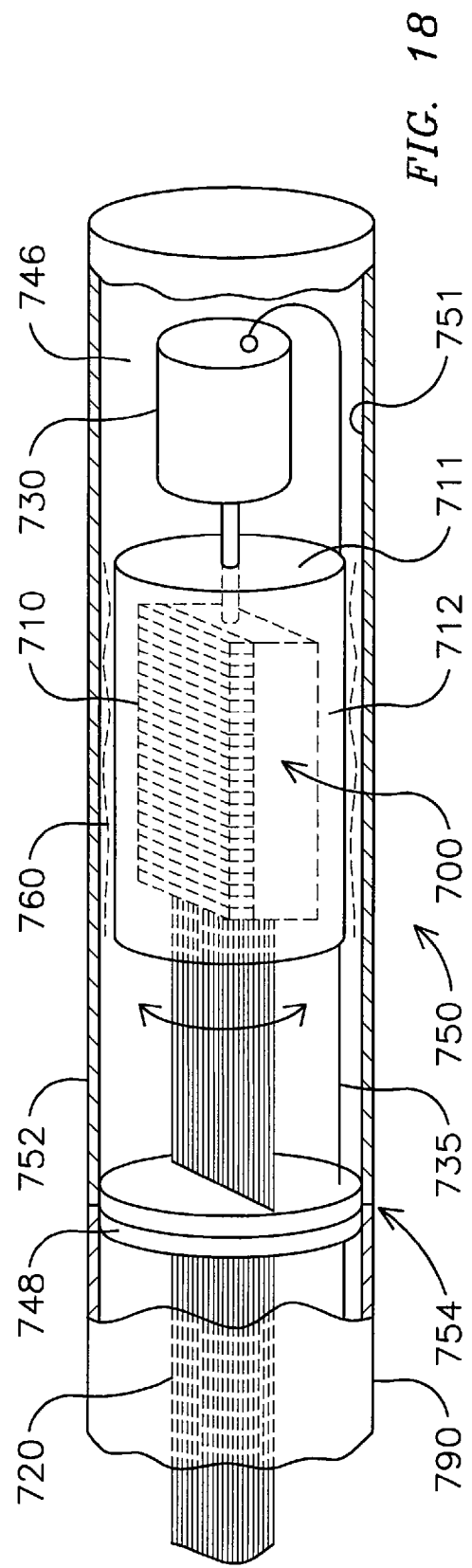
FIG. 18 is a side view with cut-away, partially internal view of a catheter tip similar to that of FIGS. 17A and 17B.

FIG. 18 provides a side view with cut-away, partially internal view of a catheter tip 750 similar to that of FIGS. 17A and 17B (with common components as identified above). However, in this embodiment, only a relatively small amount of acoustic transmission medium 760 is provided, and this surrounds the cylindrical outer surface 712 of the cylinder-shaped potting material body 711 and the inner surface 751 of catheter tip 750's outer capsule 752, remaining substantially between this and the inner surface 751 of catheter tip 750. This effectively couples acoustic energy to the catheter tip 750. Thus, the defined annular space 761 may be relatively thin and uniform, and is filled with acoustic transmission medium 760 that may be held in place during operation by surface tension. In such embodiment, acoustic transmission medium 760 need not occupy other spaces within the catheter tip 750. In variations of these embodiments the acoustic transmission medium 760 may be relatively viscous, for example between from about 1 up to about 100 cP.

Aspects of the particular embodiment of FIGS. 17A, 17B, and 18 are not meant to be limiting. Variations that include other components and arrangements are taken to be included within the scope of the invention claimed herein. For example, a transducer assembly embedded in a cylindrical (or other suitable shape) acoustically neutral potting material may be in a catheter having an integral catheter tip rather than an attachable catheter tip. As to component variations of a catheter tip that comprises a motor-driven rotatable transducer embedded in such potting material, any of the components and arrangements such as are described for other embodiments herein may be utilized (e.g., no bulkhead, with fluids passing through the catheter body for circulation purposes, bulkhead with apertures, spherical or other bearings, bushings and drive linkages as described in other embodiments above and/or selected from those known to those skilled in the art). For example, not to be limiting, a catheter tip comprising a transducer assembly in a cylindrical potting material body may utilize the acoustical coupling fluid circulation approaches such as are described herein associated with the following FIGS. 3A; 3B; 4; 5; 6; 7; 8; 9; and 13. Filling of the catheter tips with acoustic transmission medium may be provided through sealable apertures as are described herein for other embodiments. As a further example, acoustic transmission medium may be supplied during manufacture by inserting a syringe with such fluid through a hole formed by a needle attached to the syringe, and then sealing the hole so formed with an epoxy. The amount supplied may vary, such as to fill the defined space 746 of a catheter tip 750 not otherwise filled with components (referring to FIGS. 17A and 17B), or to supply a desired quantity to the defined annular space (referring to FIG. 18). However, reversibly sealable apertures also may be used. Reservoirs as described herein may be combined with the embodiments of FIGS. 17A through 22B. Also, not to be limiting, any of the thermal management approaches described in U.S. patent application Ser. No. 11/330,377, filed Jan. 11, 2006 and entitled, "Apparatuses for Thermal Management of Actuated Probes, Such as Catheter Distal Ends," which is incorporated specifically for these teachings, may be utilized with the embodiments described herein and depicted in FIGS. 17A through 22B.

A particular variation within the scope of the invention generally described for FIGS. 17A, 17B and 18 is depicted in FIG. 19. FIG. 19 provides a side view with cut-away, partially internal view of a catheter tip 750 similar to that of FIGS. 17A and 17B (with common components as identified above). However, a motor interconnect 735 is provided between transducer assembly 700 and actuator 730 Electrical power and signals are conveyed between actuator 730 (which in this embodiment is an electromechanical actuator) and a power source and controller (not shown, but as described herein above) through the transducer assembly 700 and the interconnect 720 (which, as described above, also has sufficient flexibility and/or slack to allow for rotation of the cylinder-shaped potting material body 711 encasing the transducer assembly 700). As for the interconnect 720, the motor interconnect 735 has sufficient excess length and/or flexibility so as to allow for rotation of the cylinder-shaped potting material body 711 encasing the transducer assembly 700. The variation depicted in FIG. 19 eliminates the need for electrical conduits passing adjacent to the outer surface 712 of the cylinder-shaped potting material body 711, as is depicted in FIG. 17B.

Figure 20C:
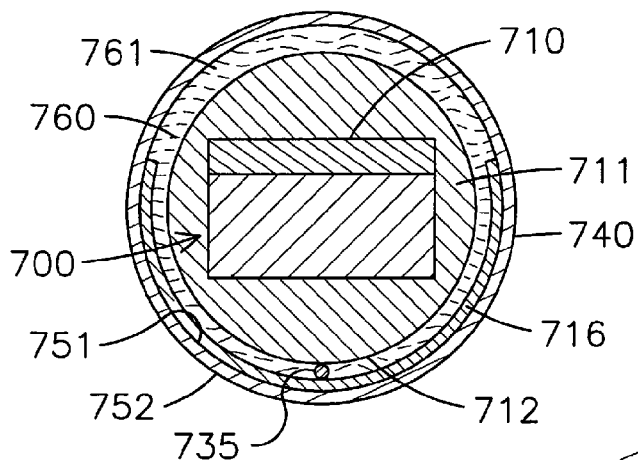
FIG. 20C is a cross-section view taken along the line C-C of FIG. 20A.

A rigid catheter tip wall may also be employed with embodiments that utilize a rotatable acoustically neutral potting material encasing a transducer assembly. The teachings above regarding such catheter tips apply to such embodiments, and FIGS. 20A-C provide one example. FIG. 20A is a side view with cut-away, partially internal view of a catheter tip 750 comprising a rigid capsule 715 made at least in part with a metal endoskeleton 716, so named because this metal is an inner, not outer layer of the capsule 715. A cut-out section 759 is provided adjacent a rotatable acoustically neutral potting material body 711 encasing a transducer assembly 700; this provides a window or window area for passage of ultrasound signals. A fluid-impermeable barrier 740 such as a polymer coating that is provided here in the form of an acoustically transparent sheath, covers the metal endoskeleton 716 and provides a fluid-transfer barrier at the cut-out section 759. Acoustic transmission medium 760 is shown filling the entire defined space 746, although in other embodiments a small amount of acoustic transmission medium may be provided to remain substantially around the outer surface 712 of the potting material body 711, similar to the approach described for FIG. 18. As to embodiments such as that of FIGS. 20A-C, it is understood that a capsule alternatively may be considered to comprise a single component or multiple components, examples of the latter comprising a metal (or other material) exoskeleton with cut-out section together with a fluid impermeable barrier covering either the cut-out section, a portion of the exoskeleton, or all of the exoskeleton.

Also viewable in FIG. 20A are two bearing surfaces 783, one disposed at a proximal end, the other at a distal end, of the potting material body 711. These bearing surfaces are part of the potting material body 711, and in various embodiments a mold for such component provides for bearing surfaces of a different diameter from the expanse of the potting material body 711 between these bearing surfaces 783. The bearing surfaces 783 are in a bearing relationship with the outer-lying inner wall of the metal endoskeleton 716, and stabilize the rotation of the potting material body 711.

FIG. 20B provides a cross-section view taken along the line B-B of FIG. 20A, and FIG. 20C provides a cross-section view taken along the line C-C of FIG. 20A. FIG. 20B shows the metal endoskeleton 716 fully encircling the defined space 746, that is filled with acoustic transmission medium 760, and also the interconnect 720 positioned therein. The fluid impermeable barrier 740, here in the form of a polymer acoustically transparent sheath, encloses the metal endoskeleton 716. FIG. 20C shows a cross-section view where the acoustic window cut-out section 759 exists. Here the metal endoskeleton 716 is cut away, and the polymer acoustically transparent sheath fluid impermeable barrier 740 in the cut-out area is in direct contact with a thin layer of acoustic transmission medium 760. The acoustic transmission medium 760 thin layer interiorly contacts the rotatable potting material body 711 that houses the transducer array 710. Although shown to fill both an inner annular space as well as to fill the immediately outer-lying void where the metal endoskeleton 716 was removed to provide the acoustic window cut-out section 759, it is appreciated that the latter space may alternatively be filled by other material, such as by a thickened section of a fluid-impermeable barrier. Both FIGS. 20B and 20C show the interconnect 735 positioned so as to not interfere with rotation of the rotatable potting material body 711.

Figure 21A:
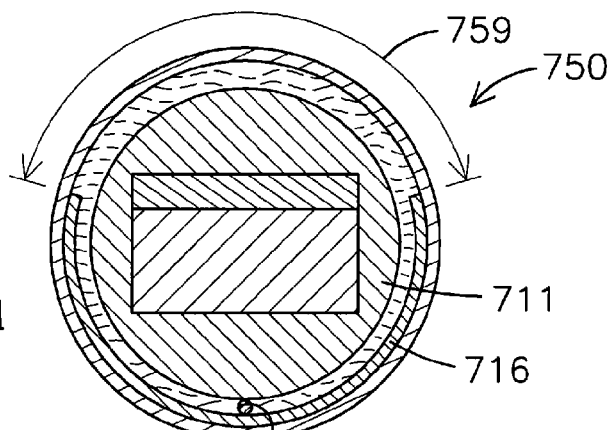
FIGS. 21A and 21B are cross-section views comparing a more uniformly cylindrical shape of a potting material body in FIG. 21A with an alternative shape in FIG. 21B.
Figure 21B:
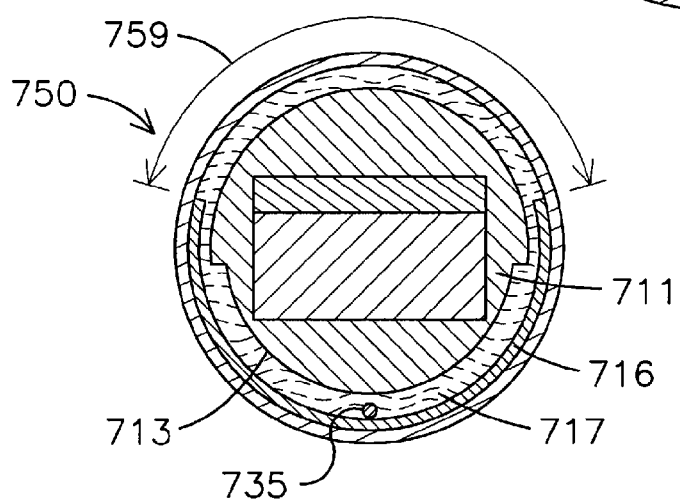

FIGS. 21A and 21B compare an alternative shape, in FIG. 21B, of a body of potting material with a more uniformly cylindrical shape in FIG. 21A. Both FIGS. 21A and 21B are cross-section views of a catheter tip 750 such as is described above, here shown comprising a metal endoskeleton 716 cut away to provide a window cut-out 759. In FIG. 21A the rotatable potting material body 711 is uniformly cylindrical. In FIG. 21B, however, the alternative cross-sectional shape of rotatable potting material body 711 comprises a recessed circular span 713 that provides additional space 717 for the interconnect 735. This body shape thus comprises a first cylindrical portion having a first diameter (that having the larger diameter) and a second cylindrical portion, identified as recessed circular span 713, having a smaller diameter than the first diameter. Thus, this rotatable potting material body 711 is not uniformly cylindrical in cross section, and demonstrates one variation in shape from a cylinder, not meant to be limiting, that is within the scope of the invention.

Figure 22:
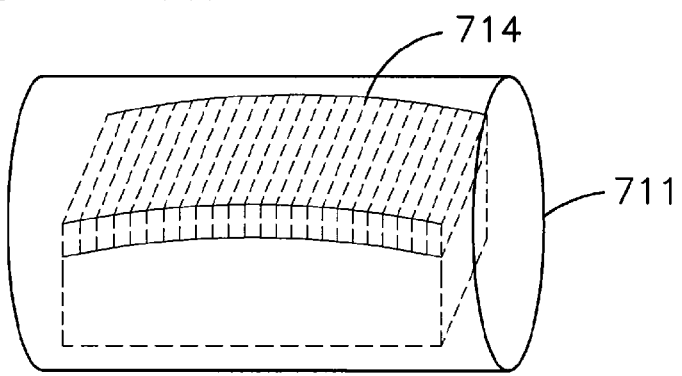
FIG. 22 provides a schematic diagram of a curved transducer array that may be provided in embodiments of the invention.

FIG. 22 provides a schematic depiction of a rotatable potting material body 711 encasing a transducer assembly 700 comprising a curved transducer array 714. This curve is not meant to be limiting. A curved transducer 714 may offer advantages with regard to beamforming and field-of-view in images, and the scope of any claim based on embodiments provided herein showing planar transducer arrays is not meant to be limited to planar transducer arrays.

Figure 23A:
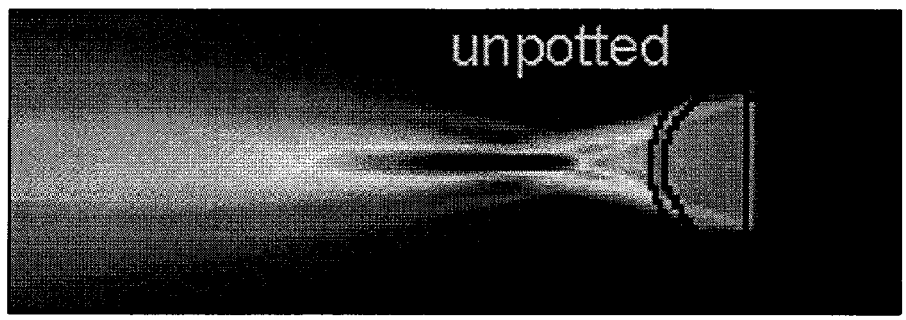
FIGS. 23A-C depict results and representations of a computer simulated comparison of an unpotted and a potted transducer assembly.
Figure 23B:
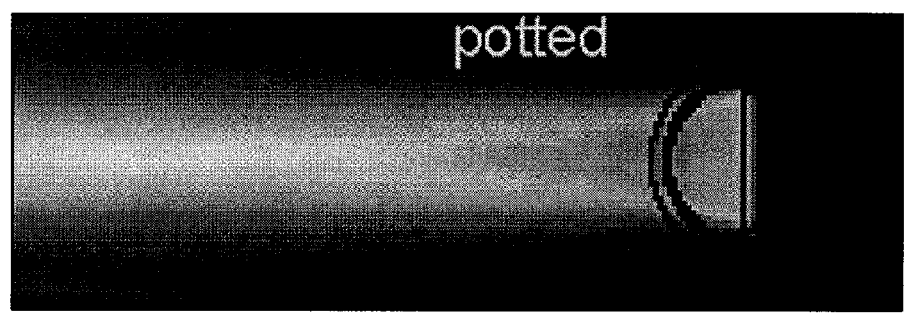
Figure 23C:
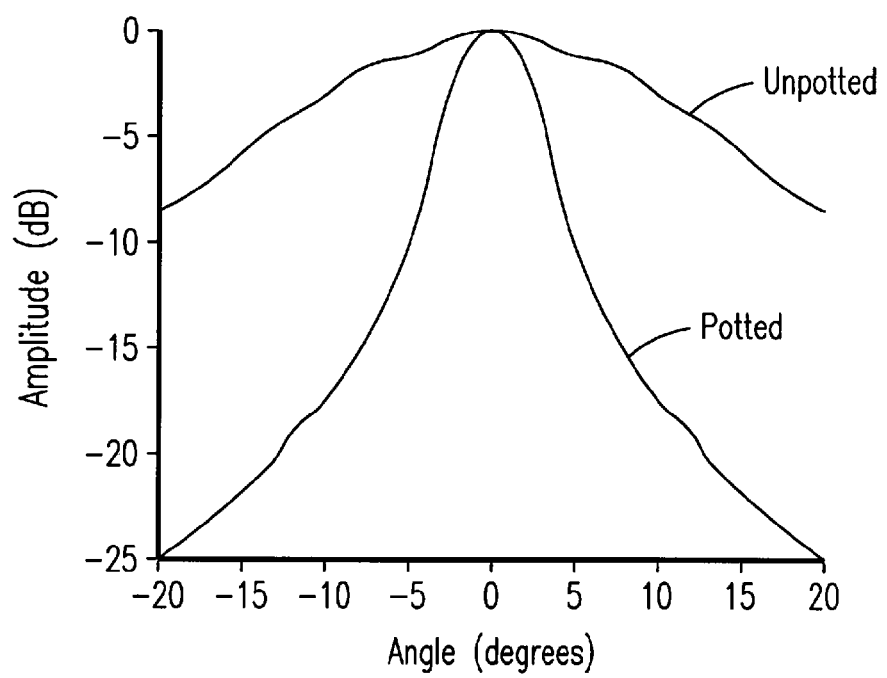

FIGS. 23A-C depict results and representations of a computer simulated comparison of an unpotted and a potted transducer assembly. The specified fluid gap for the potted transducer is 100 micrometers, the potting material is acoustically neutral, and the acoustic transmission medium has an acoustic velocity substantially lower than that of water (about 1.5 millimeters/microsecond). FIG. 23A depicts near field results for an unpotted transducer assembly, showing a focusing of the ultrasound energy compared to the pattern of FIG. 23B, which represents the potted transducer assembly. FIG. 23C compares curves for farfield transmit beams, showing that the ultrasound beam from a potted transducer assembly has less change in amplitude over +/−20 degrees of angle from the direction of transmission. Since the vast majority of the imaging occurs in the far-field, the narrower transmit beam from the potted transducer would result in far superior image resolution and contrast compared to the imaging performance of the unpotted transducer.

The above embodiments provide catheter tips with more robust, higher performance mechanically rotatable transducer assemblies that allow real-time three-dimensional (also known as 4D) ultrasound imaging from small catheter-based probes (4D ICE). The improved transducer architecture may include embedding the transducer in a cylindrical-shaped acoustically neutral potting material body, and using an acoustic transmission medium to couple acoustic energy from the transducer array to the catheter tip outer body or capsule. Not to be limiting, advantages of the approach include: 1) the cylindrical potting material body acts as a bearing to facilitate rotation of the transducer inside the catheter outer body or capsule; 2) the transducer is protected and the acoustic window in the catheter outer body or capsule is supported, increasing the robustness; 3) undesired acoustic beamforming effects are reduced due in part to the uniform layer of acoustic transmission medium; 4) biocompatibility and safety issues are simplified relative to other design approaches; and 5) improved coupling of the acoustic energy from the transducer to the catheter outer body or capsule is achieved by minimizing the presence of gas bubbles between the transducer array and the outer body or capsule.

As is further appreciated, the manufacture of a catheter tip is simplified in that bearing surfaces may be provided in the molding of the potting material body. Also, additional components or features, such as a drive linkage, or a brace or support for the interconnect, may be formed by the molding design of the potting material body. Thus, one molding/encapsulation process may replace several separate, possibly difficult process steps (difficult in part due to the small component sizes and tight tolerances).

Any of the catheter tips and catheter tip assemblies described herein may be used in catheter body/catheter tip combinations that are components of an ultrasound imaging system, which may be used in systems that further comprise an electrophysiology or hemodynamic catheter lab control and recording system, which may be utilized for guiding and/or monitoring catheter procedures, wherein the procedures include, but are not limited to, ablation procedures, other therapy procedures, and other diagnostic procedures as described herein and as known to those skilled in the art.

In operation, a catheter comprising a catheter tip fabricated as disclosed herein (such as a catheter/catheter tip combination, which may include an integral catheter comprising a tip having components arranged as for catheter tips described herein) will continuously or intermittently scan a desired volume of tissue adjacent the catheter tip while a transducer array such as 100 is rotated relative to the catheter. The rotation of the transducer array is effectuated by control of electrical current to an electromechanical actuator such as 130. It is appreciated that the scanning movement of the transducer array is achieved without rotating the catheter and without movement of the catheter in relation to the desired volume of tissue adjacent the catheter tip. This results in maintaining a precise spatial relationship between each scanned image. Data provided to the ultrasound control system may then result in generation of a series of spatially related planar tomographic images. Images taken over close time intervals may be used to develop real-time three-dimensional images. As used herein, by the term "ultrasound control system" is meant the components of an ultrasound scanner external to the catheter, which may comprise a pulse transmitter, a receiver, a scan converter, and various components for displaying and recording images. The ultrasound control system is part of an integrated catheter system as that term is used herein.

The joint between the subassembly and the flexible end of the catheter may be of any type known to those skilled in the art, including bonding together by ultrasonic welding, by IR laser beam, by glue covered by an outer biocompatible coating, by step fitting with glue, and by mechanical junctures.

It is noted that other embodiments of the invention comprise catheter tips that are produced by the methods to fabricate as described and claimed herein. Further, catheter tips comprising the elements described and arranged as provided herein are embodiments of the invention.

Also, the arrangement of components described for FIGS. 14A-H are not meant to be limiting, either for methods of fabrication nor for catheter tips (whether or not made by such methods). For example, one alternative method to fabricate a catheter tip comprises providing a polymer sheath over a rigid capsule, wherein the polymer sheath may cover only the rigid capsule or may additionally extend over a desired portion of a catheter body to which the catheter tip may be attached, comprising the steps of:

a. providing an ultrasound transducer assembly adapted for use with a catheter, the ultrasound transducer assembly comprising a proximal end and a distal end, a drive linkage to an actuator, and a transducer array, the transducer array electrically connected to an interconnect adapted for passage to or through a body of the catheter;
  b. connecting the actuator, adapted for use with the ultrasound transducer assembly, to the drive linkage;
  c. inserting the ultrasound transducer assembly and the actuator into a rigid capsule comprising a hollow body, an open proximal end adapted for connecting to the catheter, and an acoustic window along the hollow body; and
  d. inserting the rigid capsule into a polymer sheath comprising an acoustically transparent section, a closed end at its distal end and an open end at its proximal end.

The polymer sheath would cover, and/or seal around, the acoustic window of the rigid capsule in order to contain fluid that ultimately is added. Additional, optional steps, which may occur at desired times during production prior to use, may include:

e. aligning the transducer array to a desired position in relation to the acoustic window for transmission of acoustic waves through the acoustic window;
  f. filling the sheath with an acoustic transmission medium; and
  g. sealing the sheath at a point more proximal than the proximal end of the ultrasound transducer assembly, however providing for the interconnect to pass proximal from the point.

A catheter tip so fabricated may be connected to a catheter body for a desired ultrasound imaging event. Also, any of the approaches described herein for filling with an acoustic transmission medium may be employed for a catheter tip fabricated by such methods as described herein.

Also, it is appreciated that the methods disclosed herein may be used with a capsule that comprises a plastic, or a plastic type polymer that is reinforced with glass fiber, carbon fiber, or other materials, and that either has a cut-out window, is of a suitable acoustic transmission for passing ultrasound, or that comprises a section having such property and aligned over the transducer. Similarly, it is noted that the polymer sheath may comprise only a section that is acoustically transparent, or the entire sheath may be made of material that is acceptably acoustically transparent. In the former case, this section is aligned to cover the window of the rigid capsule. These alternatives may apply to all methods described herein. In another alternative method, a sheath is resilient or rigid and is used without an outer rigid capsule. This covers the transducer subassembly and is thicker and/or stronger than a polymer sheath that may be used in the above-described methods. For example, the polymer sheath may have a tensile modulus that is at least 1 GPa, and alternatively that is between about 1 GPa and 50 GPa, and more particularly between about 1.5 GPa and about 30 GPa, and more particularly, between about 2 GPa and about 15 GPa, and all subranges therebetween. Thus, for example, the sheath 140 of FIGS. 14A-H may be sufficiently resilient and/or rigid to be utilized without need for an outer capsule. The junction between a catheter tip made by this method and the distal end of the catheter body may be of any type known to those skilled in the art, including bonding together by ultrasonic welding, by IR laser beam, by glue covered by an outer biocompatible coating, or by mechanical junctions. Acoustic transmission medium may be contained in the capsule tip, such as by a seal as described herein, or may be in communication with the bore of the catheter body, as also described herein.

It is noted that some thermal sealing processes for the catheter tip may present a risk of damage to the transducer. To address and mitigate against such potential thermal damage, a cooling fluid, whether a gas or liquid, may be passed through the defined space during such thermal sealing.

Accordingly, it is appreciated that catheter tips as disclosed herein, and methods for their fabrication, provide an advance in the art of manufacture and use of catheters that comprise ultrasonic imaging capability. Catheter tips may be provided to any manufacturer of catheter bodies and catheter systems, and assembled thereto.

Also, it is appreciated that catheter tip/catheter body assemblies comprising any of the ultrasound imaging catheter tips as claimed herein are intended to be included within the scope of the invention.

Finally, aspects of the invention are viewed to include:
  1) A miniature enclosure, capsule, or package comprising a sensor (e.g., an ultrasonic transducer array).
  2) The enclosure and sensor, attached to a catheter or endoscope or laparoscope or other means for delivering the sensor to the region of interest.
  3) The enclosure and sensor are assembled and can be tested prior to integration with the catheter or endoscope. The enclosure isolates the sensor from the catheter assembly process.
  4) The sensor is an ultrasound transducer.
  5) The sensor is a single-row-or multi-row matrix ultrasound transducer.
  6) The sensor is attached to a motor or drive shaft and can be moved within the enclosure.

7) The sensor is used for static or real-time, 2D or 3D imaging.
8) The sensor, enclosure, and catheter assembly is used for intracardiac echocardiology (ICE).
9) A portion of the enclosure is transparent to the signal being sensed (ultrasound, light, etc.). The fixed sensor, or the range of motion of the movable sensor, is oriented to align the sensor with the window in the enclosure.
10) The open volume of the enclosure is filled with a specific liquid, gas, or vacuum (depending on the type of sensor and the intended use for the device).
11) The enclosure, after filling, is sealed, perhaps hermetically, so that diffusion of liquids or gases into or out of the enclosure is minimized.
12) A reservoir is provided, to accommodate thermal expansion and contraction of the filling fluid, or to provide make-up fluid to replace any that leaks or diffuses out of the enclosure.
13) The enclosure is not sealed. A means is provided for filling the enclosure before use, and perhaps for continuously flowing liquid or gas through it (or continuously pumping vacuum on it) during use.
14) The means for filling is a capillary tube through the body of the catheter or endoscope. Excess fluid is drained via the body (lumen) of the catheter or endoscope.
15) Excess fluid is vented from the enclosure into the space surrounding the device.
16) For a device used in the circulatory system, the fluid is saline solution or other bio-compatible fluid and is vented from the device into the bloodstream.
17) The enclosure comprises a structural component and a barrier or encapsulation component.
18) The encapsulation component is a thin polymeric sheath or tube. The sheath is of a material or combination of materials whose properties allow it to be both a window for the sensor (e.g., transparent to ultrasound) and a virtually impermeable barrier to the fluid that fills the sheath. For example the sheath may be a thin polyester (Mylar) tube, with a very thin coating of metal.
19) The structural component is a thin metal tube, either inside or outside the encapsulation component.
20) The structural component is the encapsulation component itself.
21) The structural component is a metal or fiber braid or mesh embedded within the encapsulation component.
22) Electrical, mechanical, and/or optical connections to the sensor and other components within the enclosure pass through the boundary of the enclosure and extend up the body of the catheter or endoscope.
23) Connection to components within the enclosure terminate at the boundary of the enclosure. A connector means is provided so that electrical, mechanical, and/or optical leads from the catheter or endoscope may be attached to the enclosure
24) Miniature hermetically sealed transducer assembly for real time 3-dimensional ("RT3D") intracardiac echocardiography.
25) Miniature hermetically sealed mechanically scanning transducer assembly for RT3D intracardiac echocardiography.
26) Thin, polymeric inner sheath containing an actuator, transducer array, and interconnect in a fluid-filled, hermetically sealed environment. The inner sheath is impermeable to the fluid within, and acts as an acoustic window.
27) Inner sheath with transducer assembly inserted into a thin, but rigid outer capsule providing mechanical support while allowing ultrasound energy to pass through an acoustic window.
28) Miniature, flexible fluid reservoir contained within the catheter and part of the transducer sub-assembly.
29) Mounting fixtures contained within the inner sheath providing structural support and maintaining proper alignment of the transducer assembly and catheter.
30) RT3D imaging catheter consisting of a catheter body with attached miniature hermetically sealed, mechanically scanning transducer sub-assembly.
31) RT3D imaging catheter consisting of a catheter body with attached miniature hermetically sealed, mechanically scanning transducer sub-assembly, comprising a biocompatible outer coating covering part or all of the catheter and transducer sub-assembly.
32) Coupling of the rigid, outer capsule to the actuator and sensor, and to the catheter, in such a way that the capsule and catheter assist in the thermal management of the actuator and sensor.
33) Hard stops to limit rotation and determine alignment of the transducer to the acoustic window [as shown in FIGS. 12A-12C].

All patents, patent applications, patent publications, and other publications referenced herein are hereby incorporated by reference in this application in order to more fully describe the state of the art to which the present invention pertains, to provide such teachings as are generally known to those skilled in the art, and to incorporate specific embodiments and teachings as are referred to herein to more fully comprehend the scope of the present invention.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim:

1. An ultrasonic imaging catheter tip assembly comprising: a catheter tip comprising an outer capsule extending from a joining end, for mating attachment to a selected catheter body, to a distal end; a transducer array disposed within a potting material body having a shape rotatable within the outer capsule and specified acoustic transmission properties; a length of interconnect comprising conductors electrically communicating with the transducer array and extending to or beyond the joining end; an actuator coupled to the transducer array or to the potting material body; and a defined annular space between the outer capsule and the potting material body, the defined annular space adapted to contain an acoustic transmission medium, wherein the potting material body has a cylindrical shape.

2. The catheter tip assembly of claim 1, wherein the length of interconnect extends beyond the joining end for a distance of at least about 80 centimeters, the distance effective to pass the interconnect through the selected catheter body to a medical imaging system that is in operative association with the selected catheter body and the catheter tip.

3. The catheter tip assembly of claim 1, wherein the actuator is positioned between the joining end and the potting material body.

4. The ultrasonic imaging catheter tip of claim 1, wherein the actuator is positioned between the potting material body and the catheter tip distal end.

5. The ultrasonic imaging catheter tip of claim 1, wherein a transducer assembly comprises the transducer array, a backing layer, an electrical connection layer, and a coupling to the actuator.

6. The ultrasonic imaging catheter tip of claim 5, wherein the actuator comprises an electromechanical actuator.

7. The ultrasonic imaging catheter tip of claim 6, wherein the electromechanical actuator comprises a drive shaft in a torque transmitting relationship with the coupling of the transducer assembly.

8. The ultrasonic imaging catheter tip of claim 1, wherein a transducer assembly comprises the transducer array, a dematching layer immediately to the posterior of the transducer array, wherein the dematching layer is comprised of a material with acoustic impedance greater than 35 Mrayl, and a coupling to the actuator.

9. The ultrasonic imaging catheter tip of claim 1, wherein the interconnect additionally comprises electrical conductors connecting to the actuator.

10. The ultrasonic imaging catheter tip of claim 1, wherein a transducer assembly comprises the transducer array, a backing layer, and an electrical connection layer, and the potting body comprises a coupling to the actuator.

11. The ultrasonic imaging catheter tip assembly of claim 1, additionally comprising an aperture at the catheter tip distal end effective for fluid passage, wherein the joining end provides for said fluid passage from the catheter body through the defined space to the aperture.

12. The catheter tip assembly of claim 1, additionally comprising a bulkhead at the joining end, wherein the interconnect extends to or through the bulkhead.

13. The catheter tip assembly of claim 12, wherein the bulkhead comprises at least one passage effective to provide fluid passage between the catheter body and the catheter tip assembly.

14. A catheter body/catheter tip combination comprising a catheter body and the catheter tip of claim 11, wherein the catheter body at its proximal end comprises an inlet for supply of a fluid-type acoustic transmission medium.

15. The ultrasonic imaging catheter tip of claim 1, the catheter tip additionally comprising a sealable aperture adapted for supplying the catheter tip with the suitable acoustic transmission medium.

16. An ultrasound imaging system comprising the ultrasonic imaging catheter tip of claim 1.

17. A system comprising the ultrasound imaging system of claim 16, and additionally comprising an electrophysiology or hemodynamic catheter lab control and recording system for guiding and/or monitoring catheter procedures.

18. A catheter body/catheter tip combination comprising a catheter body and the catheter tip of claim 1, the catheter body and catheter tip comprising a defined passageway for fluid extending to the catheter tip distal end, adapted to provide an acoustic transmission medium to the catheter tip defined space.

19. The catheter body/catheter tip combination of claim 18, the catheter body additionally comprising a return passageway extending from the catheter tip joining end to an outlet at a proximal end of the catheter body.

20. A catheter body/catheter tip combination comprising a catheter body and the catheter tip of claim 1, comprising a seal at the joining end about the interconnect, the seal comprising an opening for a reservoir, the reservoir extending proximally into the catheter body for a distance.

21. The ultrasonic imaging catheter tip of claim 1, wherein the potting material body has a shape comprising a first cylindrical portion having a first diameter and a second cylindrical portion having a smaller diameter than the first diameter.

22. The ultrasonic imaging catheter tip of claim 1, wherein the potting material body comprises a coupling, and the actuator comprises a drive shaft in a torque transmitting relationship with the coupling of the potting material body.

* * * * *